(12) United States Patent
Naujokat et al.

(10) Patent No.: US 8,979,730 B2
(45) Date of Patent: Mar. 17, 2015

(54) METHOD AND SYSTEM FOR PROVIDING BEHAVIOURAL THERAPY FOR INSOMNIA

(75) Inventors: Elke Naujokat, Eindhoven (NL); Hui Zhang, Murrysville, PA (US); Sandrine Magali Laure Devot, Aachen (DE); William Arthur Hoos, Aspinwall, PA (US); Antonius Arnoldus Johannes Rademaker, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 388 days.

(21) Appl. No.: 13/375,325

(22) PCT Filed: Jun. 1, 2010

(86) PCT No.: PCT/IB2010/052440
§ 371 (c)(1),
(2), (4) Date: Feb. 15, 2012

(87) PCT Pub. No.: WO2010/140117
PCT Pub. Date: Dec. 9, 2010

(65) Prior Publication Data
US 2012/0238800 A1    Sep. 20, 2012

Related U.S. Application Data

(60) Provisional application No. 61/184,165, filed on Jun. 4, 2009.

(51) Int. Cl.
*A61M 21/02* (2006.01)
*A61B 5/11* (2006.01)
(Continued)

(52) U.S. Cl.
CPC ............. *A61B 5/1118* (2013.01); *A61B 5/0402* (2013.01); *A61B 5/1135* (2013.01);
(Continued)

(58) Field of Classification Search
USPC ...................................................... 600/26–28
See application file for complete search history.

(56) References Cited

U.S. PATENT DOCUMENTS

| 2004/0225179 | A1 * | 11/2004 | Kaplan et al. | 600/26 |
| 2005/0143617 | A1 * | 6/2005 | Auphan | 600/26 |

(Continued)

FOREIGN PATENT DOCUMENTS

| EP | 0773504 A1 | 5/1997 |
| JP | 2000000214 A | 1/2000 |

(Continued)

OTHER PUBLICATIONS

Czeisler CS, Richardson GS. Detection and assessment of insomnia. Clinical Therapeutics [1991, 13(6):663-79; discussion 662].*

Primary Examiner — Christine Matthews
Assistant Examiner — Joshua D Lannu

(57) ABSTRACT

The disclosed system and method provide for the automatic assessment of the presence/severity of the sleep problem and its exact nature. The assessment is based on qualitative information about sleep patterns, insomnia-related factors and daytime consequences, as well as quantitative information about sleep patterns measured by a sensor. By combining the different sources of information (subjective as well as objective data), the diagnosis gives more insight into the nature of the sleep problem and is therefore more accurate. Furthermore, the disclosed system may be used to select specific components of the system that are medically relevant to the individual and therefore create a personalized program. The system teaches a selection of self-management skills that could help the individual to better cope with sleep disturbances and target those factors that maintain the problem or make it worse by a particular individual.

15 Claims, 13 Drawing Sheets

(51) Int. Cl.
*A61B 5/0402* (2006.01)
*A61B 5/113* (2006.01)
*A61B 5/00* (2006.01)
*G06F 19/00* (2011.01)
*G06Q 50/22* (2012.01)
*G09B 19/00* (2006.01)

(52) U.S. Cl.
CPC ............. *A61B5/4809* (2013.01); *A61B 5/4812* (2013.01); *A61B 5/6804* (2013.01); *A61B 5/6887* (2013.01); *G06F 19/345* (2013.01); *G06Q 50/22* (2013.01); *G09B 19/00* (2013.01); *A61B 5/4815* (2013.01); *A61B 5/7267* (2013.01)

USPC .......................................................... 600/26

(56) References Cited

U.S. PATENT DOCUMENTS

2005/0176680 A1\* 8/2005 Lalji et al. ...................... 514/58
2007/0118054 A1 5/2007 Pinhas et al.
2009/0210253 A1\* 8/2009 Ash et al. .......................... 705/3

FOREIGN PATENT DOCUMENTS

WO 2004/078132 A2 9/2004
WO 2007052108 A2 5/2007

\* cited by examiner

- Q1: How often do you exercise and how long? X times per week, Y minutes.
- Q2: Do you exercise in the 4 hours preceding your bedtime?
- Q3: How many glasses of alcohol do you drink in the evening?
  X glasses beer - wine - stronger (checkboxes)
- Q4: How many cups of caffeinated drinks do you drink per day (coffee, tea, cola)?
  X cups, y of which in the evening
- Q5: Do you take naps? X times per week, y minutes
- Q6: When do you usually nap? Before/after 4 pm (checkboxes)
- Q7: Do you smoke? X cigarettes per day
- Q8: Do you smoke before going to bed? In the middle of the night? Yes/no
- Q9: When you wake up during the night, you often:
  - Eat somethings?
  - Have something to drink?
  - Go to the bathroom?
- Q10: Do you have regular meal times?
- Q11: Do you feel sometimes too hot or too cold in your bed?
- Q12: Do you like your bedroom
- Q13: Is your sleep sometimes disturbed by noise?
- Q14: Is your sleep sometimes disturbed by light?

FIG. 12

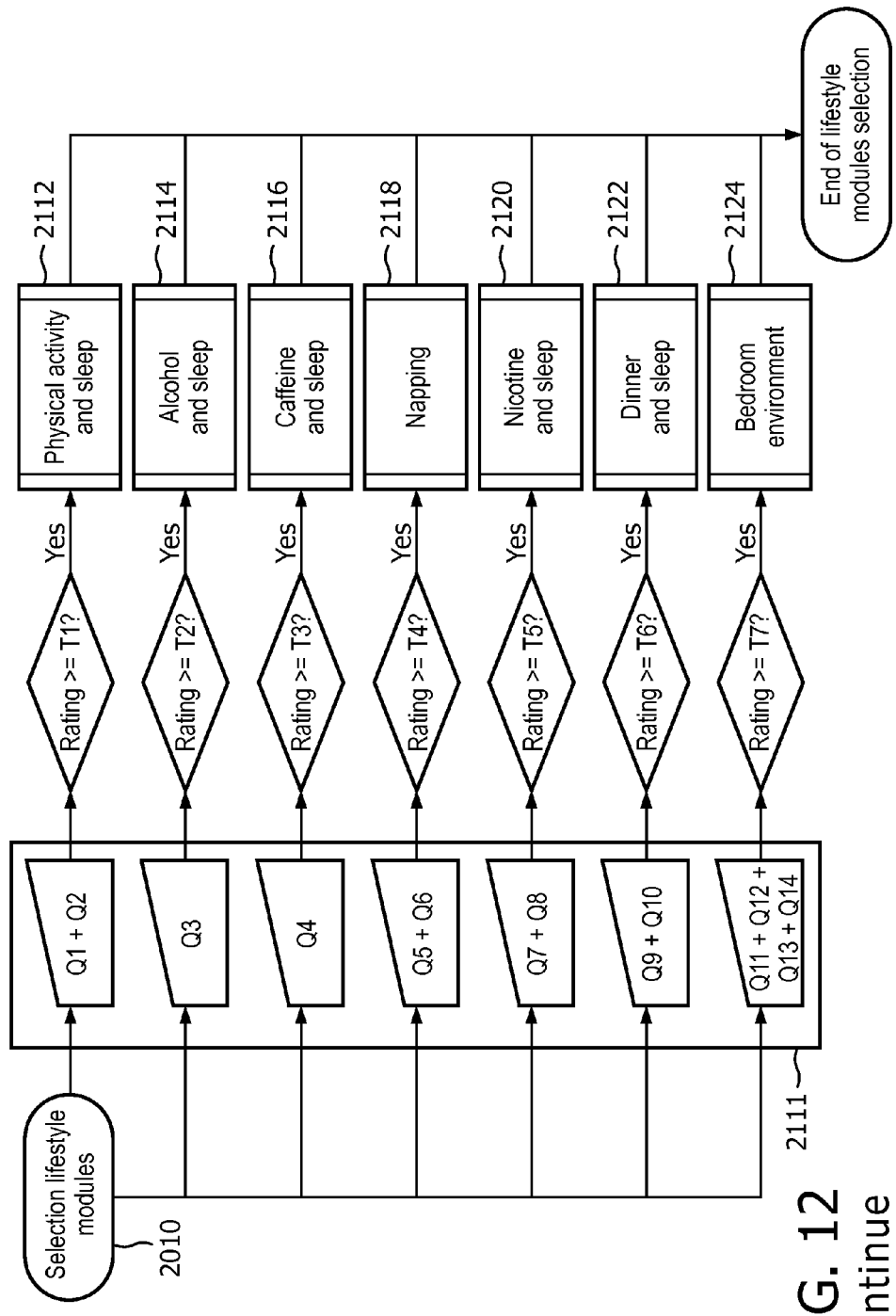
FIG. 12 Continue

METHOD AND SYSTEM FOR PROVIDING BEHAVIOURAL THERAPY FOR INSOMNIA

This application claims priority under 35 U.S.C. §119(e) to U.S. Provisional Patent Application Ser. No. 61/184,165, filed Jun. 4, 2009 entitled "System and Method for Managing Insomnia."

FIELD OF THE INVENTION

The invention relates to a system and associated method structured to facilitate cognitive behavioral therapy for a patient having insomnia.

BACKGROUND INFORMATION

Sleep disorders are common. At least 10% of the population suffers from a sleep disorder that is clinically significant and of public health importance. Insomnia is by far the most common form of sleep disturbance.

Most insomnia definitions include descriptions of sleep-specific symptoms with associated daytime complaints. Sleep symptoms typically include a difficulty initiating sleep, difficulty maintaining sleep, final awakening that occurs much earlier than desired or sleep that is non-restorative or of generally poor quality. Waking symptoms are associated with daytime complaints related to fatigue, sleepiness, mood disturbance, cognitive difficulties and social or occupational impairment.

The prevalence of isolated insomnia symptoms in the general population is approximately 30 to 50%, and approximately 9 to 15% report significant daytime impairments as a result of chronic insomnia problems. In a majority of the patient population, insomnia is treated by medication. The market for sleeping pills is about 4.6 B US$. Other forms of treatment such as sleep restriction therapy are less widespread although evidence suggests that they are more effective on the long run than pharmaceutical treatment alone.

A standard diagnostic method for assessing the nature and the severity of the sleep problem, a so-called sleep log or sleep diary, i.e. a questionnaire usually on paper, is used in most cases; also an actigraph can be used as an alternative to a sleep log.

The main drawback of this sleep log is that its accuracy is affected by a subjective bias of the patient, e.g. for patients it is often difficult to remember sleep and wake periods during the night correctly.

An automatic detection of sleep and wake stages requires the measurement of vital body signs, but unfortunately most of the existing solutions rely on adhesive electrodes, e.g. by sticking or gluing them to the patient's skin to wear electrodes, e.g. for EEG on the head. Those electrodes are obtrusive to the patient during sleeping due to the cables and recording devices, which are connected to those sensors. Additionally, there is a problem that during resting time, cables or electrodes might loose the connection, which lowers the quality of the received signal.

The diagnosis of insomnia with an automatic sleep log in a fully equipped sleep laboratory is expensive, places are not available over long time duration and thus ability for diagnosis for insomnia patients are limited.

Further, additional sensors and cabling along the patient may disturb the patient's sleep, and therefore influence the evaluation of sleep and wake stages during the night time, which leads to an influence on the sleep records and might lead to a wrong diagnosis.

U.S. Patent Application Publication No. 2004/0225179 discloses automated behavioral methods and systems for treating insomnia that use passive means for determining wake/sleep states and is incorporated herein by reference.

Insomnia is a prevalent sleep disturbance in the general population. However, in practice, patients tend to not seek treatment or are diagnosed by a non sleep specialist, e.g. a GP, without the use of a standard and proper method for assessing the nature and the severity of the sleep problem. This usually results in the underestimation of the reality of the sleep problem and/or the prescription of sleeping pills, although a drug-free therapy—the cognitive behavioural therapy for insomnia (CBT-I)—has been shown to be as effective and more sustainable. Further, a more accurate assessment and a tailored therapy may lead to a higher compliance and consequently to a better medical outcome.

An object of the disclosed concept is to provide a system structured to facilitate cognitive behavioral therapy for a patient having insomnia, the system including a communication assembly structured to provide for electronic communication, a sensor system having at least one sensor, the sensor system structured to detect sleeping activity data and to provide a sensor system signal incorporating the sleeping activity data, the sensor system coupled to, and in electronic communication with, the communication assembly, a first processing unit coupled to, and in electronic communication with, the communication assembly, the first processing unit structured to receive the sensor system signal and to convert the sleeping activity data into sleep pattern data, a second processing unit having an input assembly and structured to gather patient input data, the second processing unit coupled to, and in electronic communication with, the communication assembly, a third processing unit coupled to, and in electronic communication with, the communication assembly, the third processing unit structured to receive the sleep pattern data and the patient input data, perform an analysis thereon thereby creating a patient sleep profile, a fourth processing unit coupled to, and in electronic communication with, the communication assembly, the fourth processing unit structured to analyze the patient sleep profile and to provide a course of therapy related to the patient sleep profile, and a display coupled to, and in electronic communication with, the communication assembly, the display structured to present a user interface.

A further object of the disclosed concept is to provide a method of providing cognitive behavioral therapy for insomnia, the method including the steps of monitoring a patient's sleep utilizing a sensor system having at least one unobtrusive sensor, the sensor system structured to detect sleeping activity data, gathering patient input data, combining the patient input data and the sleeping activity data to create a patient sleep profile, analyzing a patient's sleep profile to determine a course of therapy, and presenting the course of therapy to the patient on a display.

As used herein, the term "patient" does not only apply on human beings, but also on animals. Further, the term "patient" does not mean that the respective person/animal is disease ridden, thus, also healthy people will be referred to as "patients."

The term "sleep/wake classification" refers to the classification of the epoch of interest as "wake" or "sleep," resulting from the probability of belonging to the respective class, or the classification "true" or "false" given as an output of the classifier but also refers to the display of the classifier results on a user interface or any device.

Additionally, the term "pNN50" refers to the percentage of the number of interval differences of adjacent NN-Intervals greater than 50 ms, the term "SDNN" refers to the standard deviation of all NN-Intervals, the term "SDSD" refers to the Standard deviation between distances between adjacent intervals, the term "RR_mean" refers to mean duration of the RR-Intervals, the term "HR_mean" refers to the mean heart rate, the term "LF" refers to the low frequency range, as defined by heart rate variability standards, the term "HF" refers to the high frequency range, as defined by heart rate variability standards, the term "RMSSD" refers to root mean square successive differences, and the term "HRV" refers to heart rate variability.

These and other aspects of the invention will be apparent from and elucidated with reference to the embodiments described hereinafter.

In the drawings:

FIG. 1 schematically shows the general principle of the invention;

Figure 5:
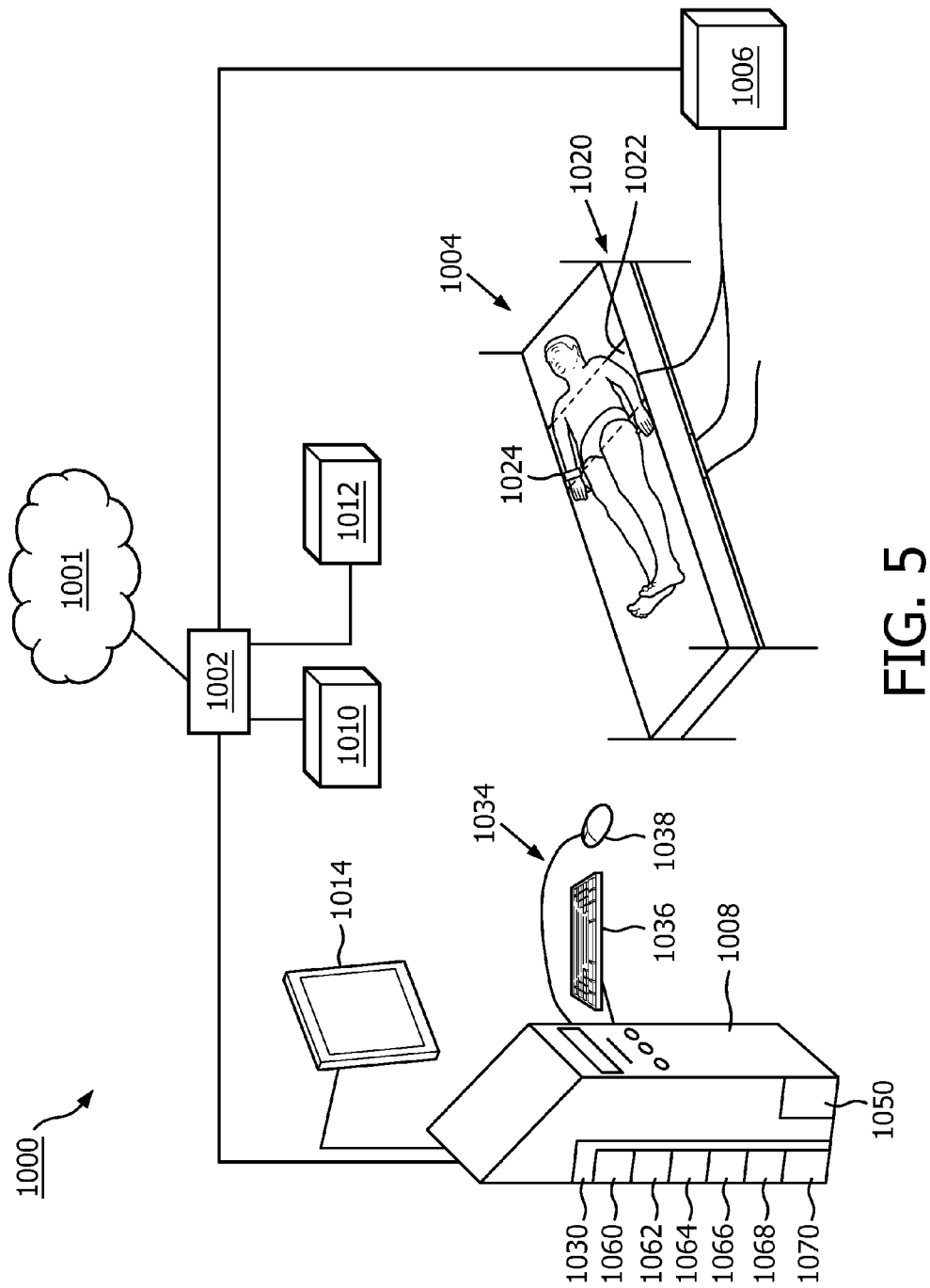
Figure 6:
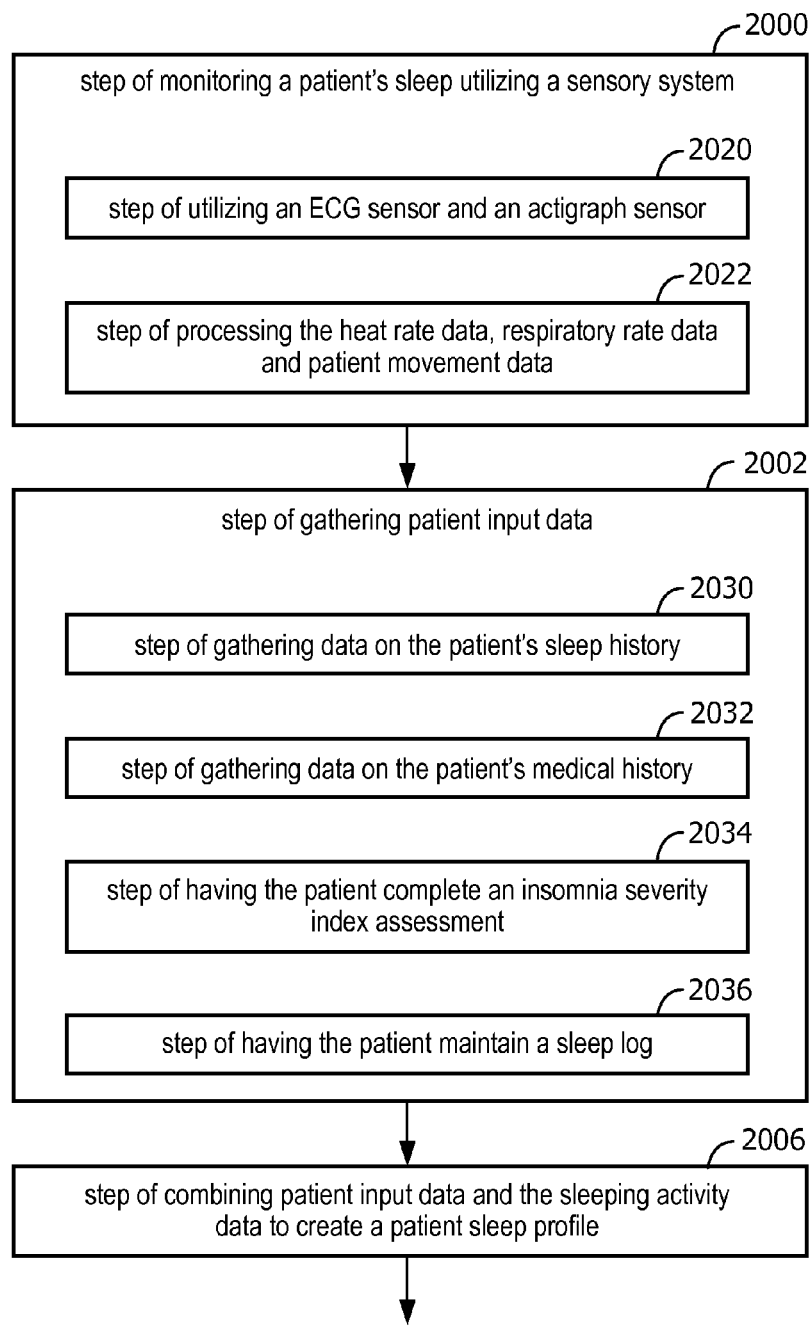
Figure 6A:
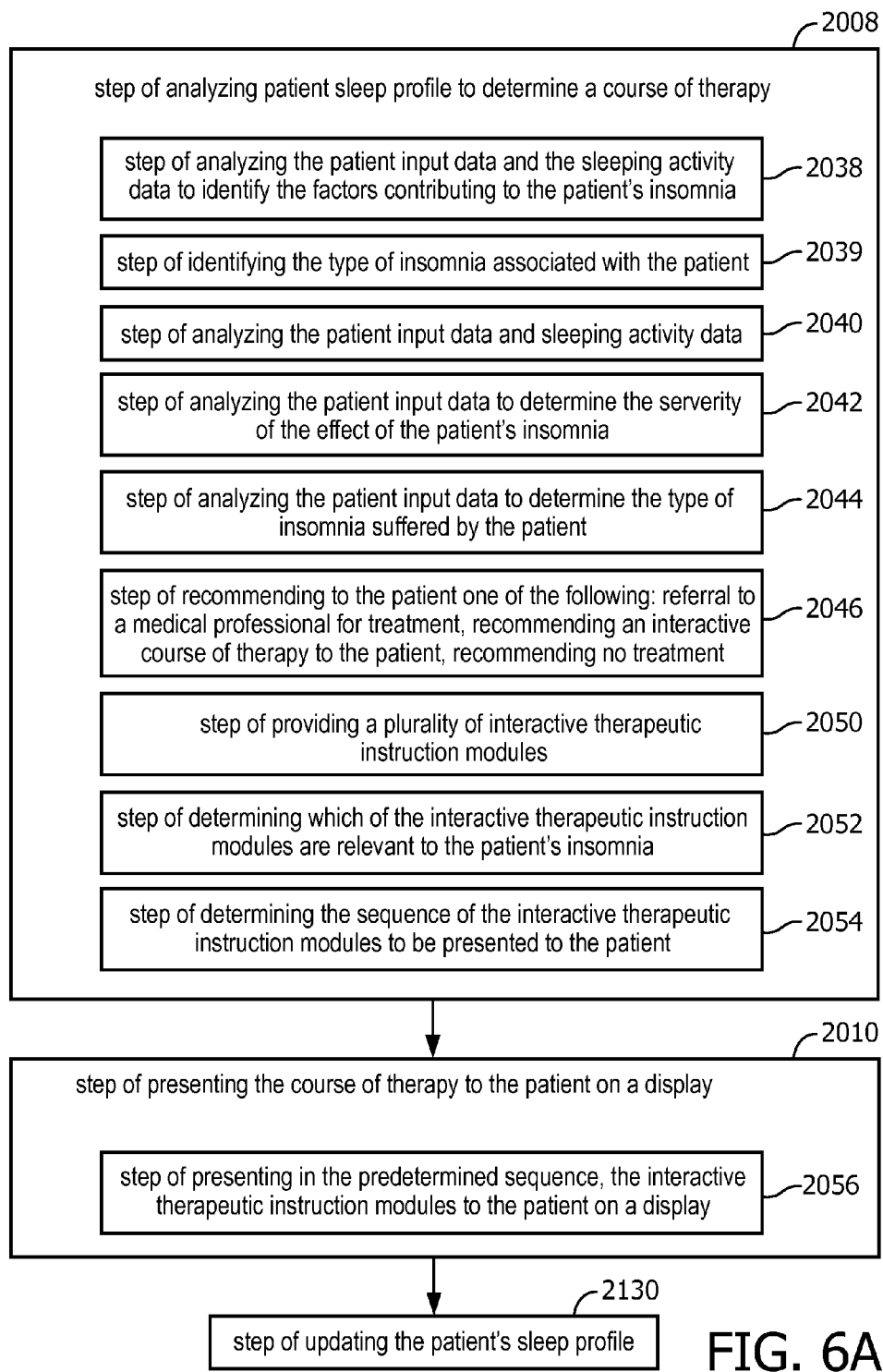
Figure 7:
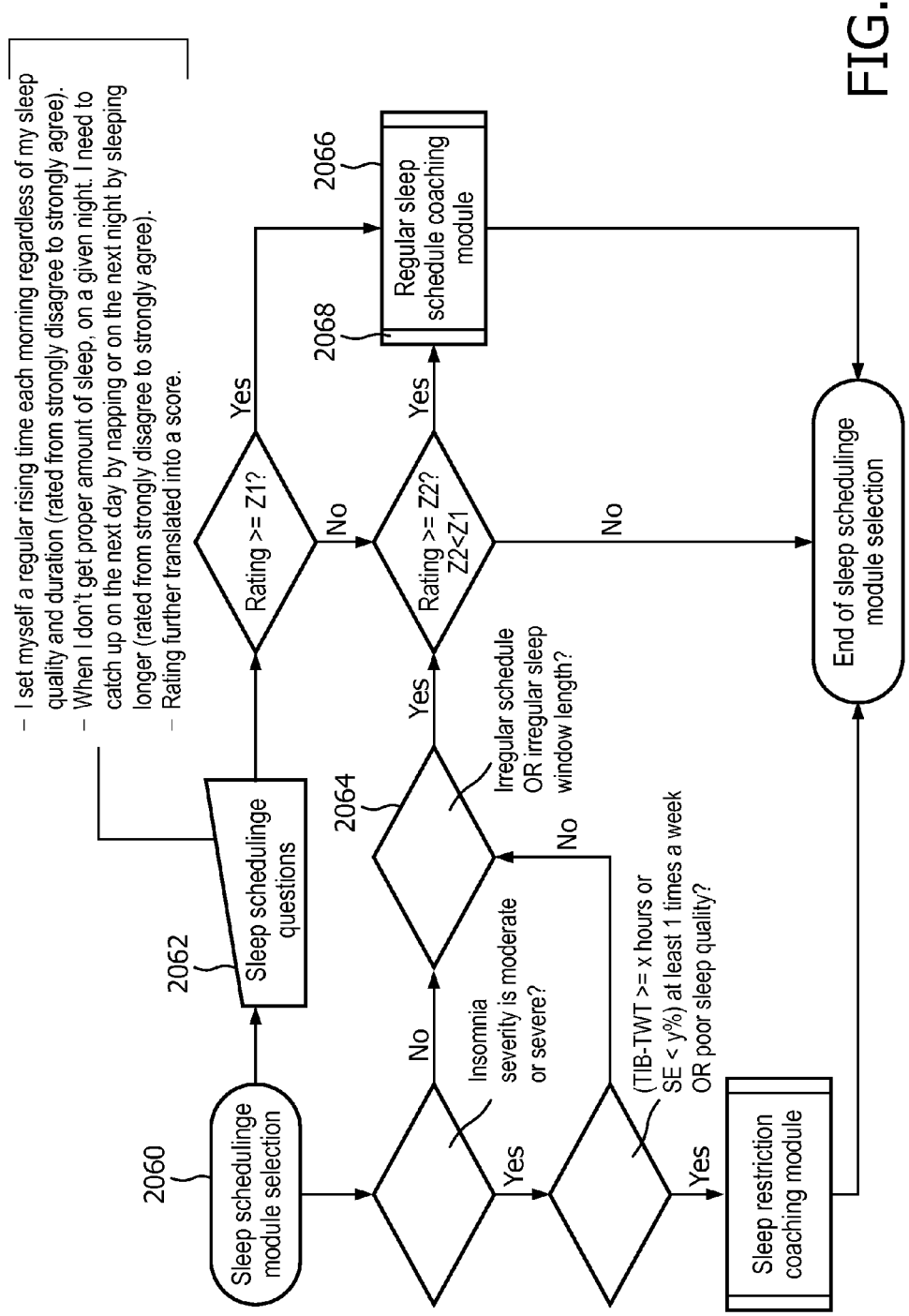
Figure 8:
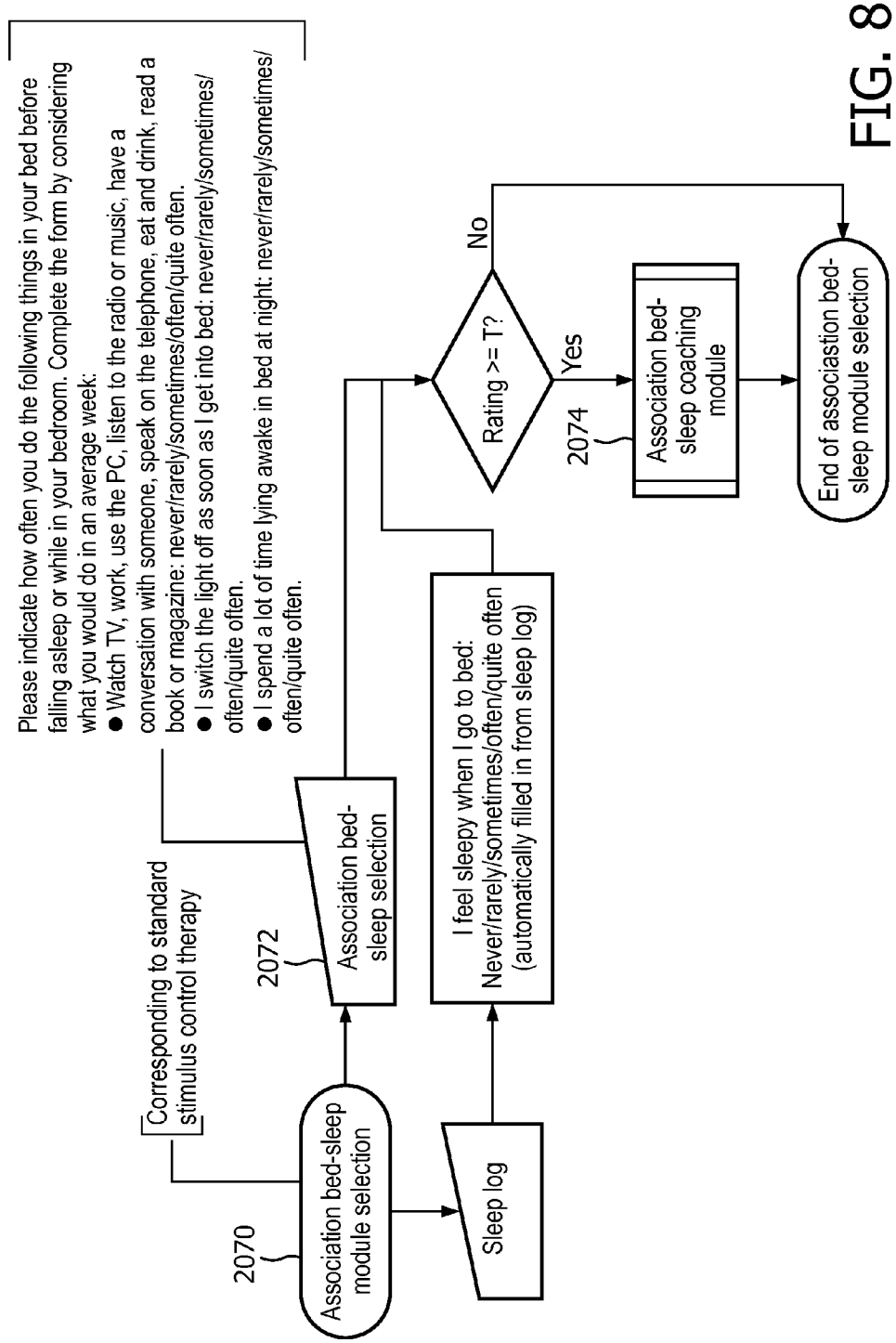
Figure 9:
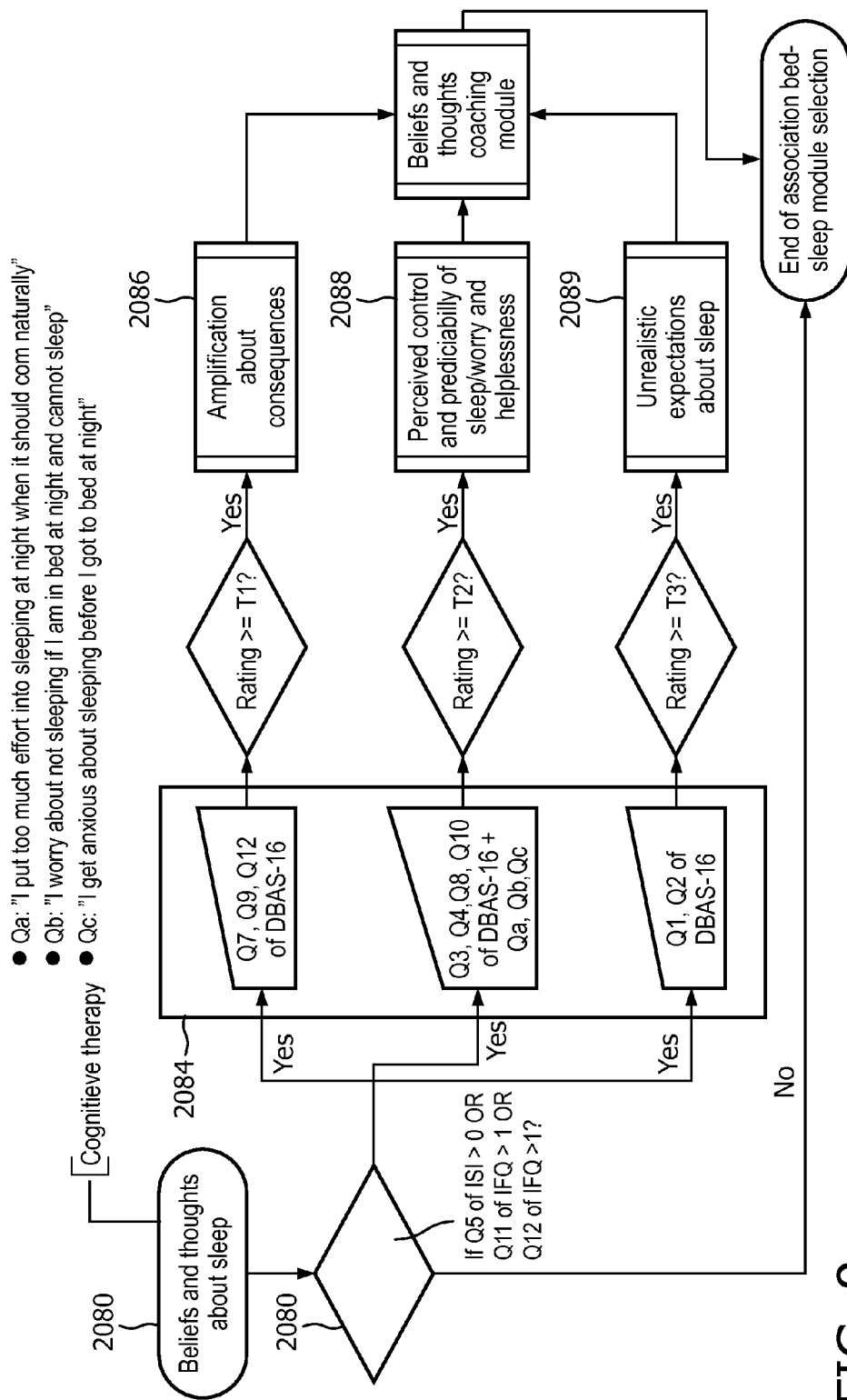
Figure 10:
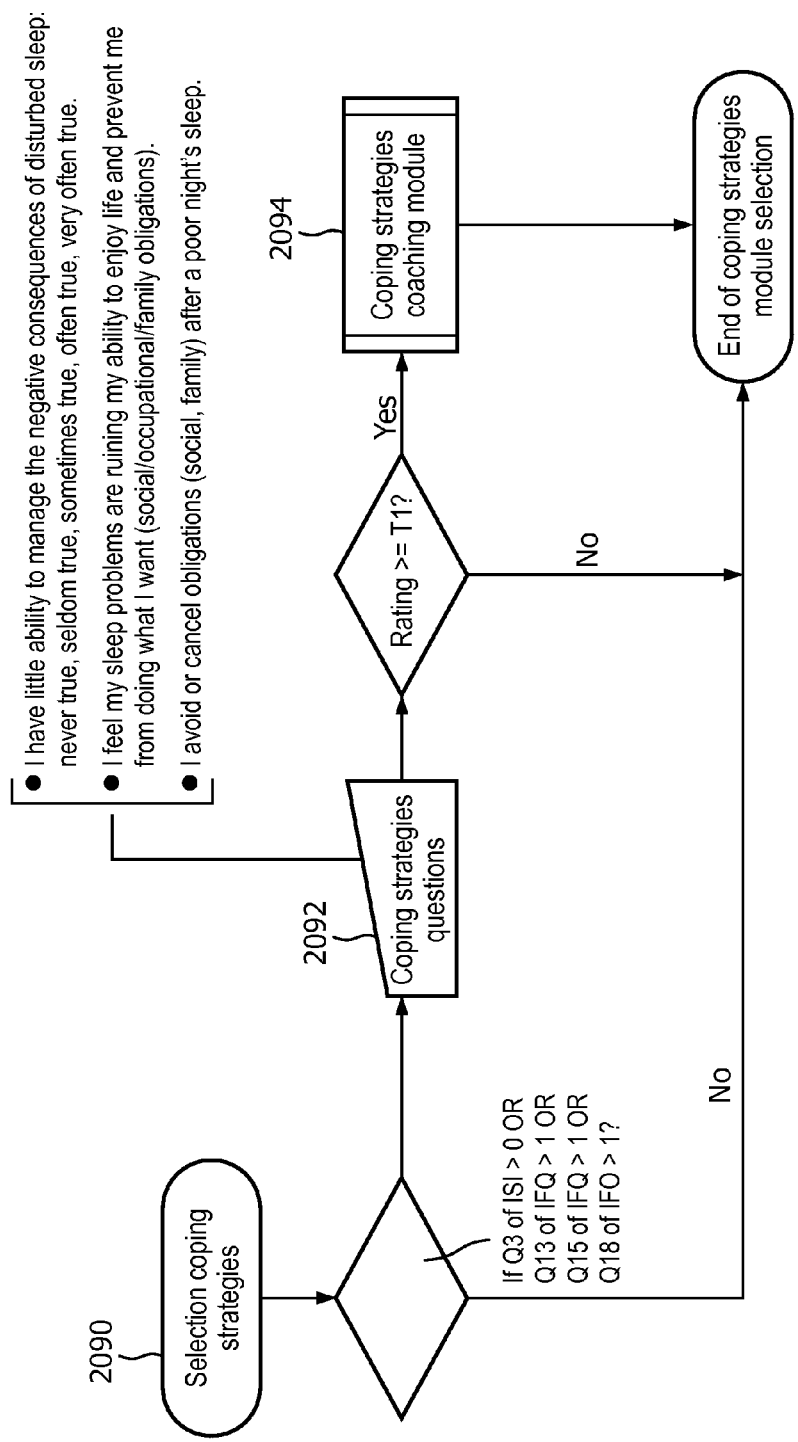
Figure 11:
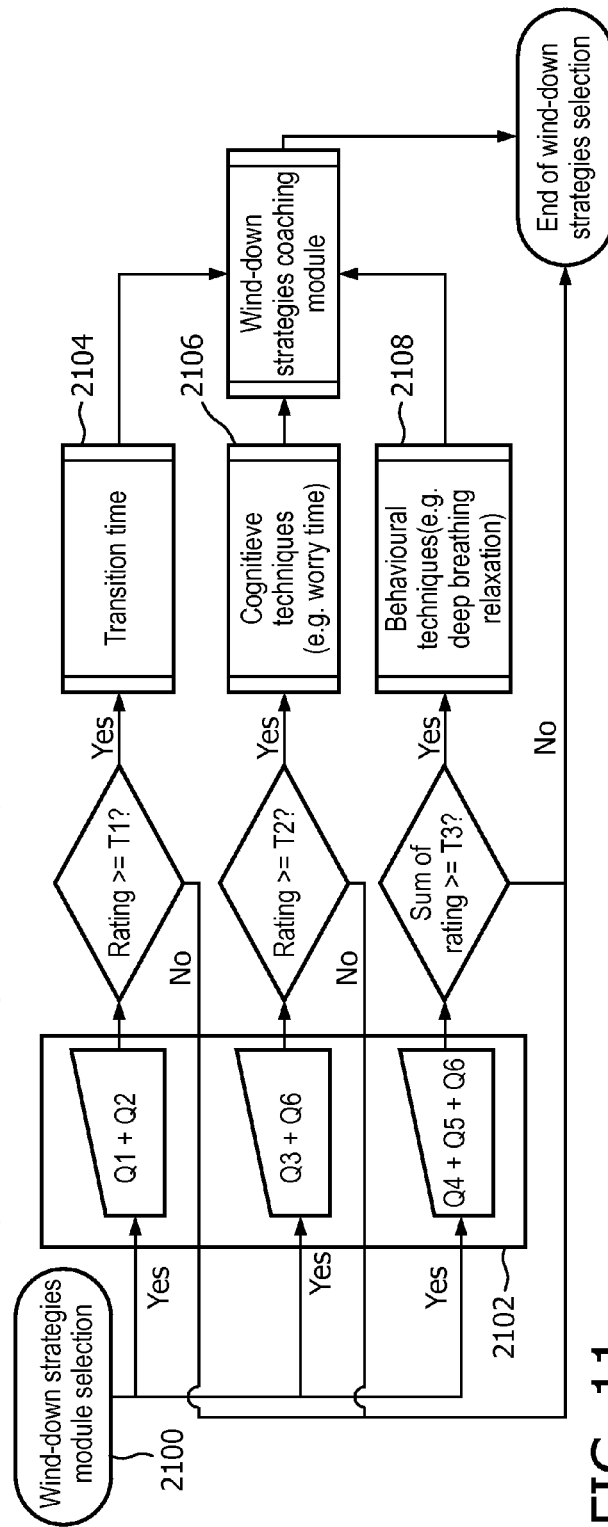

FIG. 5 schematically shows the elements of the invention;

FIG. 6 shows a schematic flowchart of the method of providing cognitive behavioral therapy for insomnia;

FIG. 7 shows a schematic flowchart related to the sleep scheduling module;

FIG. 8 shows a schematic flowchart related to the association bed-sleep module;

FIG. 9 shows a schematic flowchart related to the cognitive restructuring module;

FIG. 10 shows a schematic flowchart related to the coping strategy module;

FIG. 11 shows a schematic flowchart related to the relaxation module; and

FIG. 12 shows a schematic flowchart related to the lifestyle module.

As can be seen from FIG. 1, the system for sleep/wake classification 100 according to the preferred embodiment of the present invention comprises unobtrusive in-bed sensors for vital body sign monitoring 101 of the heart activity from the ECG, and/or the body movements from a bed foil sensor or the like as will be described in the following. A further step is the pre-processing unit 102 for filtering and artifact removal during preparation of the signals, a feature extraction unit 103 extracting in particular features from the ECG and/or the body movements signal alone or in combination, then there is a sleep/wake classifier unit 104 for classification of the sleep/wake status according to all the input features, sleep efficiency calculation unit 105 for calculating the time asleep compared to the time in bed, used as input for the patient sleep restriction algorithm, device 106 providing, for example, rules for a healthier sleep to the patient.

The output of the sleep/wake classification 104, sleep efficiency calculation 105 and sleep restriction algorithm device 106 can be used to provide feedback to the patient 107 or to the medical professional, who could also get information from additional sources like the sleep log questions for subjective parameters 109.

As for the sensor part of the proposed system, the following embodiments are possible: The sensor is a ferro-electret foil placed underneath the patient's thorax to measure heart rate, respiration and body movements.

Alternatively, in another preferred embodiment a piezo-resistive strain gauge glued onto a slat underneath the mattress in the patient's thorax region can be used to measure heart rate, respiration and body movements.

In another preferred embodiment only an ECG would be used, preferably a textile ECG integrated as a pillow and foot mat electrode in the bed.

Instead of the ferro-electret foil or the strain gauge, the ECG sensor could be combined with a respiration signal, measured with a standard (inductive or piezo-resistive) band around the thorax and/or the abdomen. This type of sensor can be also integrated into textiles (e.g. a T-shirt) to make it more unobtrusive.

Alternatively, in another embodiment instead of the ferro-electret foil or the strain gauge, the ECG sensor could be combined with an accelerometer signal. The device can be a wrist-worn device, but preferably a 2D or 3D accelerometer is placed on the patient's trunk to measure body movements. Also, this type of sensor can be integrated into textiles (e.g. a T-shirt) to make it more unobtrusive.

Figure 1:
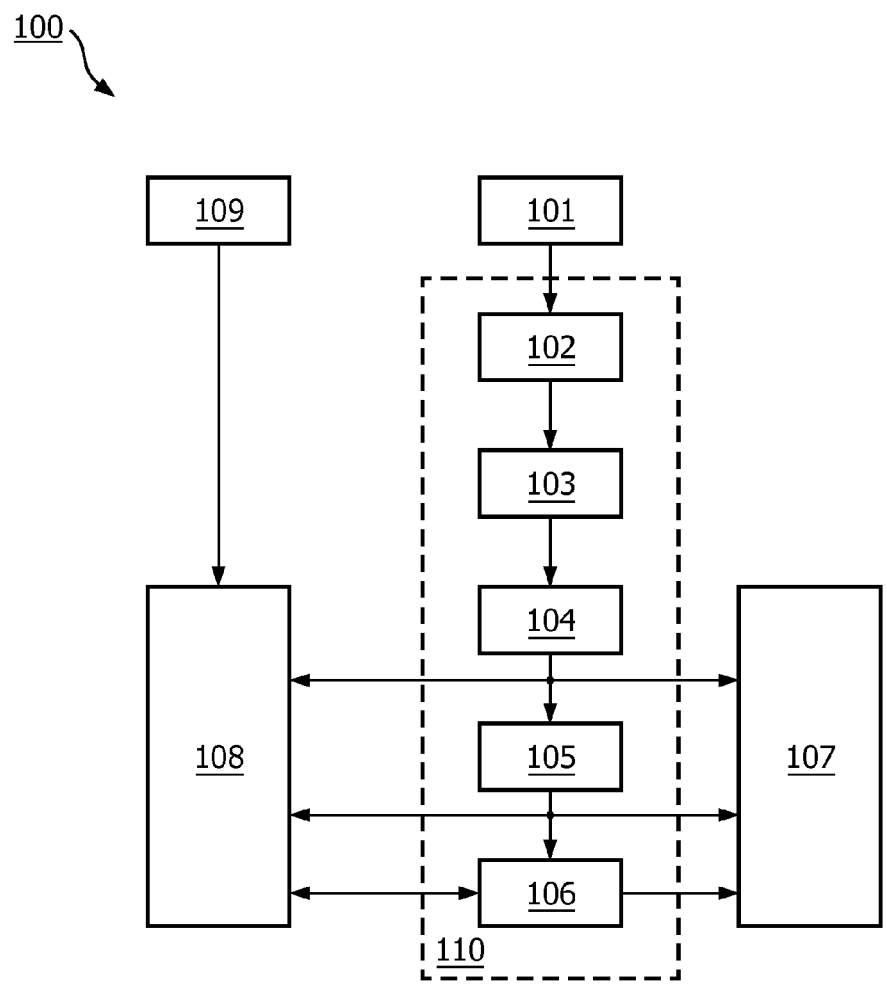

The processing unit comprises several steps as can be seen in FIG. 1. These are the preprocessing of the raw data, feature extraction and the sleep/wake classification. In the following paragraphs the different alternatives for each of these steps will be described in more detail.

The signal pre-processing device 102 of FIG. 1 includes one or more of the following steps which can be passed through serially, parallel or repeatedly:

appropriate filtering of the signal(s); and artifact removal.

In case of an ECG signal, the removal of ectopic beats can be necessary.

In case of gaps in the signal, interpolation might be necessary.

The feature extraction device 103 includes extraction of features from the ECG and a respiration signal comprising:

From the ECG, the following features are derived:

statistical heart rate variability parameters from the time domain (e.g. mean heart rate, SDNN, RMSSD etc.);

parameters from the heart rate variability (HRV) spectrum (e.g. LF, HF);

multi-scale sample entropy; and progressive detrended fluctuation analysis.

From the respiration signal-measured by the ferro-electret foil, the slat sensor or the inductive/piezo-resistive band—the spectrum is calculated and the LF and HF power are extracted as features. In addition, the mean breathing rate is determined.

Further, the feature extraction device 103 allows in case of both, the ECG signal and a respiration signal are available, to calculate the coherent power of both spectra as an additional feature. Moreover, the ratio of heart rate and breathing rate can be derived as an additional feature.

Furthermore, from the ferro-electret foil or the slat sensor signal, an activity index is derived based on large body movements.

The preferred embodiment of the present invention further suggests that for the next step—the sleep/wake classification 104—the activity index and at least one additional feature relating to the cardiac and/or respiratory status are a preferable combination as input for the classification process.

A vector, of at least one feature, and preferably all or at least a sub-set of the above-mentioned features is generated for each epoch of interest, e.g. each 1-minute segment of data.

Further, this vector is fed into a sleep/wake classifier 104 which is based on a standard pattern recognition approach with supervised learning, as will be described in FIG. 3. For the classifier, the following approaches can preferably be used:

Bayesian linear or quadratic discriminant classifier;
support vector machine;
k-Nearest-Neighbour (kNN) method;
Neural Network; and
Hidden Markov Model.

The parameters of the classifier are trained on a large database of representative data.

In order to receive the patient's input regarding the subjective questions in the sleep log, Insomnia Severity Index, Insomnia Frequency Questionnaire, or other assessments and to give feedback to him, the input unit and the display unit are preferably combined in the preferred embodiment of the present invention in one user interface device 107. This device can be a normal laptop PC, a tablet PC with a touch screen, a handheld device such as a PDA or a mobile phone. Depending on the processing power of this device, the processing unit can also be part of this device. The feedback to the patient can contain one or more of the following parameters: time in bed, total sleep time, total wake time, sleep efficiency, sleep latency, number and durations of awakenings, or a simplified hypnogram.

The feedback to the medical professional can be given via the same user interface 108. In another embodiment, there is a download procedure to transfer the patient's data from the patient user interface to the physician's PC (e.g. via a USB cable, via Bluetooth, ZigBee or any other communication standard or device). In yet another embodiment, the patient's data can be (automatically) sent to the physician via the Internet or GSM, UMTS, EDGE, GPRS, or any other Internet or mobile phone standard or system.

The feedback to the medical professional should contain all of the above-mentioned parameters. Furthermore, it should also contain the patient's answers to the subjective sleep log questions so that he can compare the subjective and objective data which gives him important information for the appropriate therapy approach. This is, for example, especially important in case of sleep-state misperception, a type of insomnia where objective sleep data reflect a normal sleep pattern but the patient himself does not recognize that he has slept.

Figure 2:
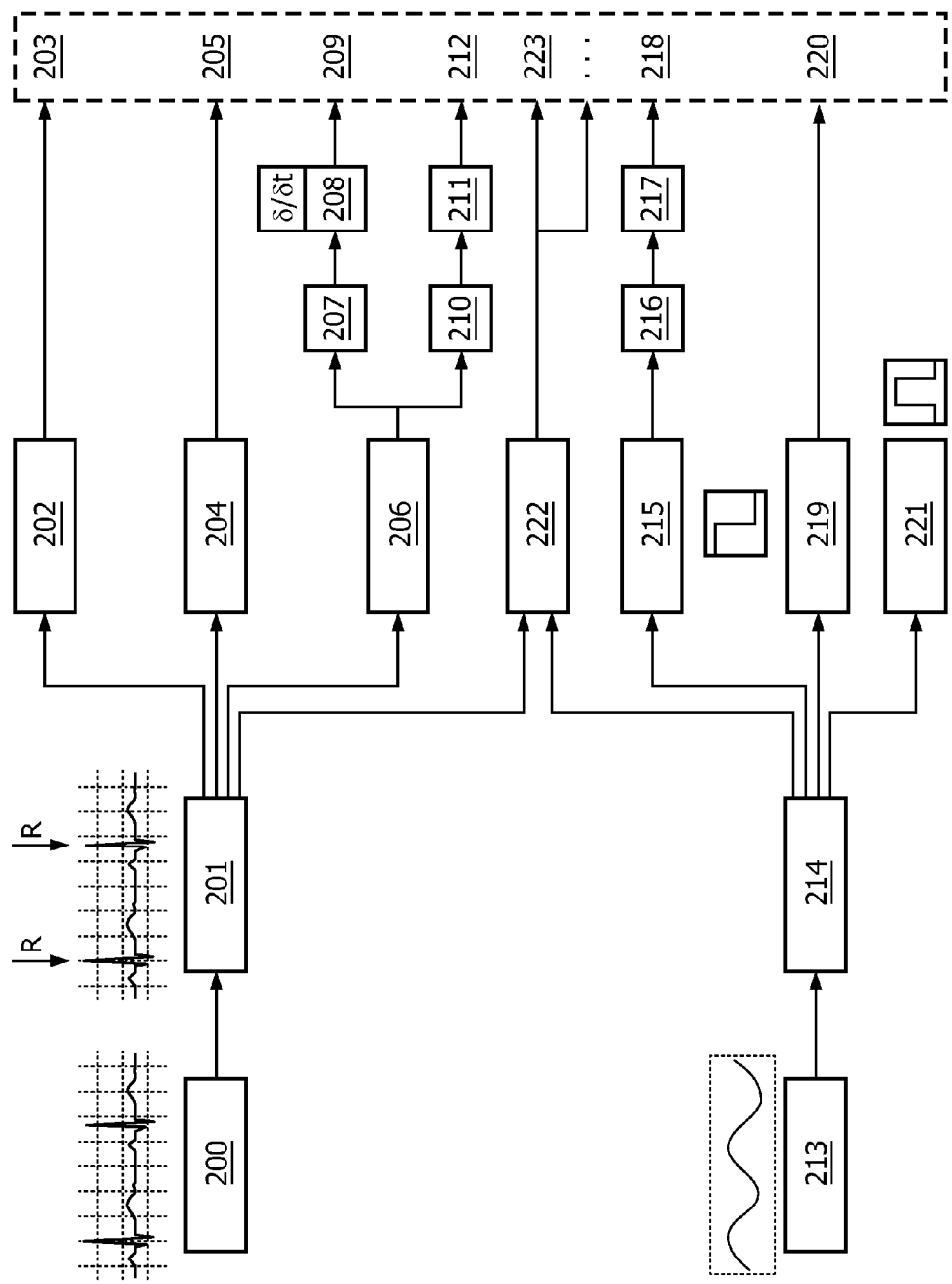
FIG. 2 shows a schematic flowchart of the feature extraction method of a first preferred embodiment of the invention.

As can be seen in FIG. 2, the ECG signal provided by an ECG sensor 200 undergoes a pre-processing 201, wherein the preprocessing consists in R-peak detection, ectopic beat removal, linear interpolation and resampling at a predefined frequency, preferably at 4 Hz. The resulting RR-interval series is then considered and heart rate variability parameters, according to the standard, are assessed in frequency and time domains. First the power spectrum calculation 202 over a predefined time period, preferably a 5-minute segment of the time series, centered on the one-minute epoch of interest, is computed using preferably an autoregressive model with advanced detrending. Alternatively, other methods based on Fourier analysis, time-frequency distributions, time-varying autoregressive modeling is available. In the two last cases, the power spectral estimation is updated on a shorter time scale, e.g. every new detected R-peak of the ECG.

The power spectrum in the low-frequency band LF preferably at 0.04-0.15 Hz and in the high frequency band HF preferably at 0.15-0.4 Hz are used to define the spectral features in 203: the power is normalized according to LF_norm=LF/(LF+HF) and LF/HF ratio is calculated. Furthermore, the RR-interval series time statistics over a predefined time period, preferably a 5-minute segment, in 204 provides the resulting time domain features in 205, e.g. pNN50 (percentage of the number of interval differences of adjacent NN-Intervals greater than 50 ms), SDNN (standard deviation of all NN-Intervals), SDSD (standard deviation of successive differences between adjacent intervals), RMSSD (root mean square successive differences), RR_mean (mean duration of the RR-Intervals) and HR_mean (mean of the instantaneous heart rate).

Non-linear parameters are also extracted from the RR-interval time series in 206 by the application of two methods. The first non-linear calculation method used in 207 is progressive detrended fluctuation analysis which allows to gradually integrate the signal before detrending over windows of length 64. Further, the partial sums of the squared signal are then considered and this provides the resulting differentiated time series in 208 from which we extract a new feature 209, defined as the maximum value over the considered epoch, preferably a one-minute epoch but which can be any predefined epoch duration.

The second non-linear calculation method applied to the RR-interval series provides the multiscale sample entropy. Firstly, the series is coarse-grained at scales 1 and 2 in 210 and 5-minute segments are considered. The sample entropy (hereafter called sampen) is calculated in 211 at several levels from 1 to 10 Hence, the following features in 212 are provided: sampen_scale1_k, for levels k=1 to 10 and sampen_scale2_k, for levels k=1 to 10.

As can be seen in the lower part of FIG. 2, the bed foil signal provided by bed foil sensor 213 is undergoing a pre-processing 214 which consists of noise reduction and calibration. The use of low pass filtering 215 leads to the breathing signal. Peak identification on this signal allows to deduce the breath interval series, which is also linearly interpolated and resampled at a predefined rate, preferably at 4 Hz in 216. The power spectrum 217 is computed using preferably an autoregressive model with advanced detrending. The power spectrum is then split and normalized in 218 in the low-frequency band LF (0.04-0.15 Hz) and in the high frequency band HF (0.15-0.4 Hz), which are used to define the spectral features LF_norm_respi and LF/HF ratio_respi. Besides, the detection of small and large energy artefacts in 219 allows to define a heuristic activity index over one-minute epochs, also used as a feature in 220. Further, the band-pass filtering in 221 delivers the so-called ballistocardiogram, which represents the mechanical heart activity. This signal could be an interesting alternative to the ECG signal to get the heart rate variability signal. Finally, the RR-interval and the breath interval series are combined in 222 by estimating the squared coherence function over 5-minute epochs centred on the one-minute epoch of interest. This coherence function is multiplied by the autospectrum of the RR-interval series and integrated along the frequency axis. The resulting feature in 223 is the amount of coherent power in %. We could also think of other features assessing the cardiopulmonary coupling, like the RR-interval/breath interval ratio.

Figure 3:
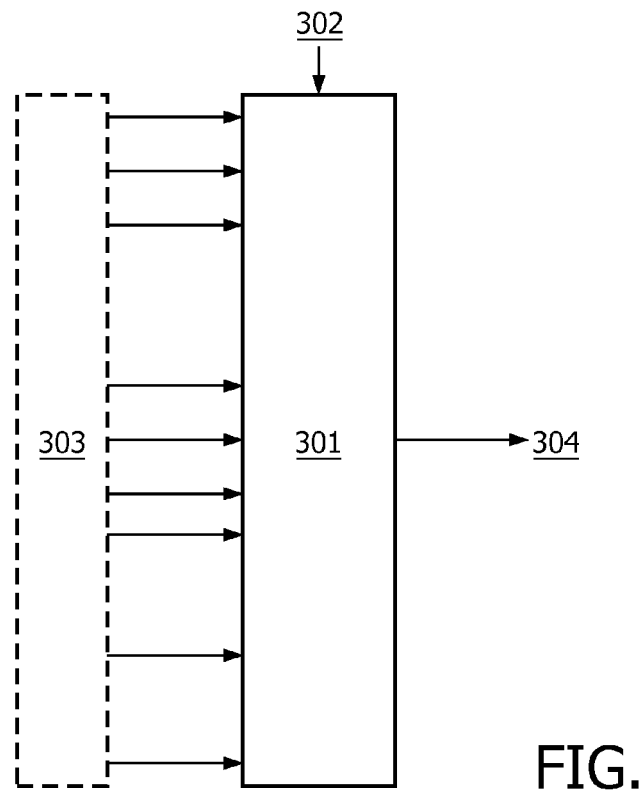
FIG. 3 shows a schematic flowchart of the sleep/wake classification method of a first preferred embodiment of the invention.

As can be seen in the right part of FIG. 2, a preferred embodiment contains the features 203, 205, 209, 212, 223, 218, 220, which form the components of the feature vector used in the classification process which is further described in FIG. 3.

FIG. 3 is a preferred embodiment of the method for sleep/wake classification. Step 303 represents information coming from the feature extraction process providing a vector with at least one element, which belongs to the test data set. The decision is based on a supervised learning classifier 301, which is trained with a training data set 302. The classifier 304 decides on the basis of a Bayesian linear or quadratic discriminant classifier, a support vector machine or the k-Nearest-Neighbour (kNN) classifier and with a supervised learning approach based on the training data set, whether the patient is awake or asleep. The more representative the training data are, the better the accuracy and performance of classification 304.

The sleep restriction therapy is a non-pharmacological method that can be used to treat insomnia either alone or in combination with pharmacological treatment. There is a natural tendency among poor sleepers to increase the amount of time spent in bed in an effort to provide more opportunity for sleep, a strategy that is more likely to result in fragmented and poor quality sleep.

The sleep restriction therapy consists of curtailing the amount of time spent in bed to the actual amount of time asleep. Time in bed is subsequently adjusted on the basis of the sleep efficiency calculation for a given period of time, which is usually the preceding week. For example, if a person reports sleeping an average of 6 hours per night out of 8 hours spent in bed, the initial prescribed sleep window would be 6 hours.

The subsequent allowable time in bed by about 15 to 20 minutes for a given week when sleep efficiency exceeds 90%, decreased by the same amount of time when the sleep efficiency is lower than 80% and kept stable when the sleep efficiency falls between 80 and 90%. Alternatively, a therapist may set the upper limit at 85% sleep efficiency. Adjustments are made periodically, for example weekly, until optimal sleep duration is achieved. Variations in implementing this procedure may involve changing the time in bed on the basis of a moving average of the sleep efficiency, for example, of the past three to five days, or changing it on a weekly basis regardless of change of the sleep efficiency. This procedure improves sleep continuity through a mild sleep deprivation and a reduction of sleep anticipatory anxiety. To prevent excessive daytime sleepiness, the time in bed should not be reduced to less than five hours per night.

Figure 4:
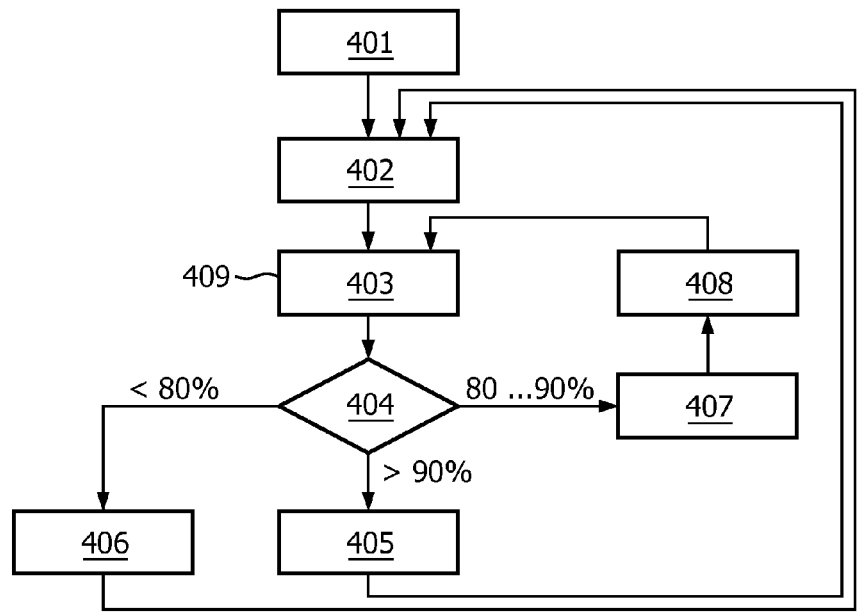
FIG. 4 shows the sleep restriction algorithm based on the method of the present invention.

As can be seen in FIG. 4, there is a preferred embodiment of the sleep restriction therapy method based on the sleep efficiency calculation which is provided by the present invention.

In the first step 401, the medical practitioner initializes wake-up-time and go-to-bed time. In step 402 data is collected for five days, which also includes information from questionnaires.

In step 403 the mean sleep efficiency of the last five days is calculated. In step 404 a case decision is made, deciding whether the mean sleep efficiency is lower than 80%, 80 to 90% or greater than 90%.

In case the mean sleep efficiency is lower than 80%, in step 406, the patient is asked to shorten the time in bed by 15 minutes, in case the mean sleep efficiency is greater than 90%, in step 405 the patient is asked to prolong time in bed by 15 minutes. The process recontinues at step 402 with the collection of sleep information for the next five days. In case the mean sleep efficiency is between 80 to 90%, in step 407 positive feedback is given to the patient and in step 408 the wake-up-time and the go-to-bed time will be kept for one more day and the process continues at step 403.

The disclosed concept may also be identified as a system 1000 structured to facilitate cognitive behavioral therapy for a patient having insomnia and may utilize the method set forth below. Prior to discussing the system 1000 and method, the following definitions are noted.

As used herein, "unobtrusive sensor" means a sensor that is either not attached directly to the patient's body, e.g. by an adhesive, or is wireless. A sensor that is not coupled to the patient's body includes, for example, a ferro-electret foil disposed immediately adjacent, or in contact with, the patient's thorax is an "unobtrusive sensor" because it is not attached to the patient and the patient may move freely. Other "unobtrusive sensors" include a piezoresistive strain gage coupled to the patient's bed, an ECG sensor embedded in fabric, e.g. a pillow, bedding, pajamas, nightcap or a radar/video system structured to detect movement. An "unobtrusive sensor" that may be coupled to the patient's body includes any small/light sensor that may be installed on a bracelet or similar construct. One example of such an unobtrusive sensor is an accelerometer. Any sensor that has a wire extending between the patient and a device is not an "unobtrusive sensor."

As used herein, "sleeping activity data" is data, and preferably biometric data, representing a measurable action, whether voluntary or involuntary, that is an indication of a patient's state of consciousness, i.e. asleep or awake.

As used herein, an "assessment" is one or more questions/statements answered on a scale, e.g. 1 to 5, days per week, very sleepy to wide awake, etc. Such answers are converted to "points," e.g. sleepy=1 point, wide awake=5 points. If more than one question is related, the points may be combined into a score. The act of combining points may be simple addition, but may also include a multiplier for synergistic combinations. For example, an assessment may include the following three questions/statements: Rate the severity of (1) difficulty falling asleep, 1=none, 5=severe, (2) difficulty staying asleep, 1=none, 5=severe, and (3) how many cups of coffee do you drink after 6:00 PM. Here, the "points" associated with questions (1) and (2) may be combined through simple addition, whereas the "points," e.g. number of cups of coffee consumed, may be a multiplier. Further, as is known, the final combined score for an assessment is typically compared to one or more predetermined threshold values associated with that assessment. For example, one assessment may determine the level or severity of the patient's insomnia and another assessment may determine the type of insomnia associated with the patient. Named assessments include, but are not limited to: Epworth Sleepiness Scale (ESS), Pre-Sleep Arousal Scale, Sleep Disturbance Questionnaire, Sleep Hygiene Practice Scale, Caffeine Knowledge Quiz, The Sleep Behavior Self-Rating Scale, The Glasgow Content of Thoughts Inventory, The Glasgow Sleep Effort Scale, Pittsburgh Sleep Quality Index (PSQI), and the Multidimensional Fatigue Inventory (MFI).

As used herein, a "threshold value" may also be a range of values. That is, a "threshold value" may exist as a maximum value, a minimum value, or a range of (un)acceptable values.

As shown in FIG. 5, the system 1000 structured to facilitate cognitive behavioral therapy for a patient having insomnia includes a communication assembly 1002, a sensor system 1004, a first processing unit 1006, second processing unit 1008, third processing unit 1010, a fourth processing unit 1012, and a display 1014. The communication assembly 1002 is structured to provide for electronic communication between the components identified above. That is, each component is coupled to, and in electrical communication with, the communication assembly 1002. The communication assembly 1002 and the components may be wirelessly coupled to the various components. The communication assembly 1002 is preferably coupled to, and in electrical communication with, an electronic communication network 1001, such as, but not limited to, the Internet.

The sensor system 1004 has at least one sensor 1020. The sensor system 1004 is structured to detect sleeping activity data and to provide a sensor system signal incorporating the sleeping activity data. As used herein, "sleeping activity data" includes at least, heart rate data, respiratory rate data and patient body movement data. As is known, data from such sensors 1020, e.g. motion data detected by an actigraph and heart rate data detected by an ECG, may be combined to determine, or estimate, if the patient is awake or asleep. It is again noted that the ECG sensor associated with the disclosed method is an unobtrusive sensor, i.e. a sensor incorporated into the patient's clothes rather than a traditional ECG having wires/leads coupled to a sensor adhered to the patient's skin. Other sensors that may be used include, but are not limited to inductance plethysmography sensors structured to detect respiratory effort and Emfit foil, structured to measure ballistocardiography (cardiac activity, respiratory activity and body motion activity).

The sensor system 1004, that is each at least one sensor 1020, is coupled to, and in electronic communication with, the communication assembly 1002. Each at least one sensor 1020 is an unobtrusive sensor structured to produce a sensor signal having at least one feature, as set forth above. The at least one sensor 1020 may be, but is not limited to, an ECG sensor 1022 and/or an actigraph sensor 1024. The ECG sensor 1022 is structured to detect heart rate data and respiratory rate data. The heart rate data and respiratory rate data being a feature incorporated into an ECG sensor 1022 signal. The actigraph sensor 1024 is structured to detect patient body movement data. The patient body movement data being a feature incorporated into an actigraph sensor 1024 signal. Specific types of the at least one sensor 1020 are discussed above. Thus, the at least one sensor 1020 may be a single accelerometer, a single actigraph, etc.

Each processing unit, i.e. the first, second, third and fourth processing units 1006, 1008, 1010, 1012, each include operational elements such as, but not limited to, a programmable logic circuit (PLC) and a communication system (neither shown), as is known in the art. The operational elements of each processing unit 1006, 1008, 1010, 1012 may also include a memory device (not shown) such as, but not limited to, random access memory (RAM), read-only memory (ROM), flash memory, and/or a hard drive, which may be a disk or solid state. The memory device is structured to store one or more sets of executable instructions, hereinafter routines 1030, as well as collected data, other data provided with the routines 1030, and data downloaded via the electronic communication network 1001. As is known, any data stored on each processing unit 1006, 1008, 1010, 1012 may be communicated to a remote location, such as, but not limited to a medical professional's office, via the communication assembly 1002 and electronic communication network 1001. Similarly, data and/or routines 1030 may be downloaded to each processing unit 1006, 1008, 1010, 1012 from a remote location, such as, but not limited to a medical professional's office, via the communication assembly 1002 and electronic communication network 1001. It is understood that the operational elements of each processing unit 1006, 1008, 1010, 1012 operate cooperatively to perform any function that the processing unit is structured to accomplish.

The operational elements of each processing unit 1006, 1008, 1010, 1012 are preferably disposed in a housing (shown schematically). The operational elements of two or more processing units 1006, 1008, 1010, 1012 may be disposed in a shared housing (not shown) and may operate cooperatively. That is, for example, routines 1030 for each processing unit 1006, 1008, 1010, 1012 may be stored on a single storage device. At least one processing unit 1006, 1008, 1010, 1012, however, has a PLC that is not a general purpose PLC. Preferably, the first processing unit's 1006 PLC is not a general purpose PLC.

The first processing unit 1006 corresponds to the pre-processing unit 102 described above. That is, the first processing unit 1006 is structured to perform the steps associated with the pre-processing unit 102 described above. The first processing unit 1006 is coupled to, and in electronic communication with, the communication assembly 1002. The first processing unit 1006 is structured to receive sensor system signal, via the communication assembly 1002, and to convert the sleeping activity data into sleep pattern data. Sleep pattern data includes a patient's time in bed, a patient's total sleep time, a patient's total wake time, a patient's sleep efficiency, a patient's sleep onset latency, a patient's awakenings after sleep onset and a patient's snooze time. As used herein, "time in bed" means the time the patient spends in bed, whether asleep or awake. As used herein, "total sleep time" is that portion of the time in bed that the patient is asleep. As used herein, "sleep onset latency" is the time between the patient getting into bed and first falling asleep. As used herein, "wake after sleep onset" is that portion of the time in bed that the patient is awake from the first time he/she fell asleep to the moment he/she finally woke up in the morning. As used herein, "snooze time" is the duration from the final awakening to the time when the patient gets out of bed. As used herein, "total wake time" is that portion of the time in bed that the patient is awake. As used herein, "sleep efficiency" is the ratio of total sleep time to time in bed. As used herein, "awakenings after sleep onset" is the number of times that the patient wakes after first falling asleep. Thus, the first processing unit 1006 is structured to process the heart rate data, respiratory rate data, and patient body movement data to determine at least one of the patient's time in bed, the patient's total sleep time, the patient's total wake time, the patient's sleep efficiency, the patient's sleep onset latency, the patient's awakenings after sleep onset and the patient's snooze time.

The second processing unit 1008 corresponds to the user interface device 107 described above. That is, the second processing unit 1008 is structured to perform the steps associated with the user interface device 107 described above. The second processing unit 1008, preferably, includes the display 1014. The second processing unit 1008 includes a routine 1030 that is structured to present the user interface 108 on the display 1014. The second processing unit 1008, preferably, includes an input assembly 1034 having one or more input devices such as, but not limited to, a keyboard 1036 and a mouse 1038 (or trackball, or touch screen, or any other device that provides a mouse-like functionality). As is known, the patient may enter patient input data via the input assembly 1034 and the user interface 108. The user interface 108 is structured to present one or more assessments, discussed below, and to allow the user to input data into a sleep log. The second processing unit 1008 is coupled to, and in electronic communication with, the communication assembly 1002.

The third processing unit 1010 corresponds to the feature extraction unit 103, the sleep/wake classifier unit 104 and the sleep efficiency calculation unit 106 described above. That is, the third processing unit 1010 is structured to perform the steps associated with the feature extraction unit 103, the sleep/wake classifier unit 104 and the sleep efficiency calculation unit 106 described above. The third processing unit 1010 is coupled to, and in electronic communication with, the communication assembly 1002. The third processing unit 1010 is structured to receive the sleep pattern data and the patient input data, via the communication assembly 1002, and to perform an analysis thereon. The analysis creates a patient sleep profile. As used herein, a "patient sleep profile" is a collection of data including objective data, such as the patient body movement data, and subjective data, such as the patient input data. The patient sleep profile includes the patient's sleep history, sleep patterns, qualitative and quantitative measures of insomnia, identification of insomnia-related factors and identification of daytime consequences of insomnia Daytime consequences of insomnia include, but are not limited to, poor daytime energy, poor cognitive functioning (e.g. concentration, focus, attention, and memory) and poor mood and motivation.

A qualitative measure of insomnia includes, but is not limited to, a subjective estimation of sleep quality e.g. poor to excellent or as on a Likert scale of 1 to 10. A quantitative measure of insomnia includes, but is not limited to, the Insomnia Severity Index (ISI) score, discussed in detail below, subjective and objective estimates of Sleep Onset Latency, Wake After Sleep Onset, and Snooze time. Such quantitative measures of insomnia may be compared to a standard threshold, e.g. the Sleep Onset Latency threshold is set to 30 minutes. Such a comparison may be used to assess the type of sleep disturbance (problem with sleep initiation, sleep maintenance or early awakenings, etc.). Further, subjective and objective estimates of Sleep Efficiency, may be compared to standard thresholds (e.g. 90%) to assess whether or not the patient sleeps in a consolidated way.

The third processing unit 1010 is structured to send the sleep pattern data, the patient input data and the patient sleep profile to a medical professional via the electronic communications network 1001.

The fourth processing unit 1012 corresponds to the sleep restriction algorithm device 106 described above. That is, the fourth processing unit 1012 is structured to perform the steps associated with the sleep restriction algorithm device 106 described above. The fourth processing unit 1012 is coupled to, and in electronic communication with, the communication assembly 1002. The fourth processing unit is structured to analyze the patient sleep profile. The analysis performed by the fourth processing unit 1012 is discussed below. The fourth processing unit 1012 is further structured to provide a course of therapy related to the patient sleep profile. That is, the fourth processing unit 1012 includes a memory device 1050 having stored thereon a plurality of interactive therapeutic instruction modules 1060, 1062, 1064, 1066, 1068, 1070.

The therapeutic instruction modules 1060, 1062, 1064, 1066, 1068, 1070 are, generally, associated with insomnia related factors. Insomnia related factors include, but are not limited to behavioral and cognitive factors. For example, behavioral factors include, but are not limited to, sleep restriction, scheduling of bedtime and wake time. Behavioral factors may note a change in the patient's pattern, irregular sleep/wake times and/or when a patient enters in a compensatory strategy, e.g. going to bed earlier and/or sleeping in and/or napping so as to compensate for a bad night's sleep. Behavioral factors also include stimulus control, i.e. association of bed-sleep or when the conditioning between bed and sleep ceases. That is, bed and bedtime become cues for activity rather than cues for sleep. For example, the patient may lie awake in bed, which confuses the connection in the brain between bed and sleep and maintains wakefulness. Other behavioral factors include the patient's pre-sleep routine and other habits that may impact sleep, e.g., alcohol, caffeine, nicotine, dinner habits, bedroom environment, etc. Cognitive factors include, but are not limited to, the patient's mind racing during the night, i.e. hyperarousal at bedtime, and/or worries, anxiety about sleep, e.g., amplification about consequences of insomnia, perceived control and predictability of sleep, unrealistic expectations about sleep.

Each interactive therapeutic instruction module 1060, 1062, 1064, 1066, 1068, 1070 contains three parts: (1) therapeutic advice, given on the first day a patient accesses a module, (2) the general information delivered in daily tips on the remaining days of the module, and (3) a goal setting section, accessible on the first day a patient accesses the module. The therapeutic advice consists of recommendations/interventions which are based on the standard CBT-I. The therapeutic advice and daily tips targets those factors that maintain the problems or make them worse by a particular patient and may be related to the goals identified by the patient. That is, while the general, or global, goal is to improve sleep, the patient may know of a specific problem and identify a specific goal related to that problem. For example, the patient may wish to learn to fall asleep more easily and/or learn to fall back to sleep more easily after waking in the middle of the sleep cycle. Alternatively, the patient may wish to learn how to feel more refreshed in the morning, improve their daytime energy, improve their daytime performance, improve their cognitive functioning (concentration, focus, attention and memory) and/or improve their mood and motivation. Or, as another alternative, the patient may wish to identify their actual sleep pattern or determine how many hours of sleep they have during the night. The coaching and/or other advice may be related to the global goal or one or more of the more specific goals.

The fourth processing unit 1012 is further structured to organize the selection and order of the therapeutic instruction modules based upon the patient's sleep profile. Finally, the fourth processing unit 1012 is structured to present the organized therapeutic instruction modules on the display 1014.

The display 1014 is coupled to, and in electronic communication with, the communication assembly 1002. The display 1014 is structured to present the user interface 108, discussed above, as well as any other information.

Prior to discussing the method associated with the system 1000, the following assessments are noted. The assessments, or individual portions thereof, are used during the various analyses discussed below. One known assessment is the Insomnia Severity Index (ISI) which includes the following questions/statements:

Insomnia Severity Index

| | None | Mild | Moderate | Severe | Very Severe |
|---|---|---|---|---|---|
| 1. Please rate the current severity of your insomnia. | 0 | 1 | 2 | 3 | 4 |
| a. Difficulty falling asleep | ☐ | ☐ | ☐ | ☐ | ☐ |
| b. Difficulty staying asleep | ☐ | ☐ | ☐ | ☐ | ☐ |
| c. Problem waking up too early | ☐ | ☐ | ☐ | ☐ | ☐ |
| | Very Satisfied | A Little | Somewhat | Much | Very Dissatisfied |
| 2. How satisfied/dissatisfied are you with your current sleep pattern | 0 | 1 | 2 | 3 | 4 |
| | ☐ | ☐ | ☐ | ☐ | ☐ |

-continued

| | Not At All Interfering 0 | A Little 1 | Somewhat 2 | Much 3 | Very Much Interfering 4 |
|---|---|---|---|---|---|
| 3. To what extent do you consider your sleep problem to interfere with your daily functioning (e.g., daytime fatigue, ability to function at work, daily chores, concentration, memory, mood, etc.)? | ☐ | ☐ | ☐ | ☐ | ☐ |
| | Not At All Noticeable 0 | Barely 1 | Somewhat Noticeable 2 | Much 3 | Very Much Noticeable 4 |
| 4. How noticeable to others do you think your sleeping problem is in terms of impairing the quality of your life? | ☐ | ☐ | ☐ | ☐ | ☐ |
| | Not At All Worried 0 | A Little 1 | Somewhat Worried 2 | Much 3 | Very Much Worried 4 |
| 5. How worried/distressed are you about your current problem? | ☐ | ☐ | ☐ | ☐ | ☐ |

Another known assessment, the Insomnia Frequency Questionnaire (IFQ), includes responses indicating the number of days per week the patient suffers from the indicated symptoms and includes the following questions/statements:

| Insomnia symptoms | Number of nights per week |
|---|---|
| 1. I took medication at bedtime to sleep | 0 1 2 3 4 5 6 7 |
| 2. I took medication in the middle of the night to go back to sleep | 0 1 2 3 4 5 6 7 |
| 3. It took more than 30 minutes to fall asleep at the beginning of the night | 0 1 2 3 4 5 6 7 |
| 4. I was awake for more than 30 minutes in the middle of the night | 0 1 2 3 4 5 6 7 |
| 5. I woke up at least 30 minutes before my planned (or desired) rise time and was unabe to resume sleep | 0 1 2 3 4 5 6 7 |
| 6. My sleep was fragmented (woke up 3 or more times) | 0 1 2 3 4 5 6 7 |
| 7. I felt unrefreshed or tired when I got up to start my day | 0 1 2 3 4 5 6 7 |
| 8. I struggled for >30 minutes to get myself out of bed to start the day | 0 1 2 3 4 5 6 7 |
| 9. I got less than 6.5 hours of sleep | 0 1 2 3 4 6 6 7 |
| 10. I got sufficient amount of sleep | 0 1 2 3 4 5 6 7 |
| Daytime symptoms related to poor sleep | Number of days per week |
| 11. During the day, I was concerned that I might not sleep well that night | 0 1 2 3 4 5 6 7 |
| 12. During the day I was concerned that my poor sleep might affect my performance, well-being, or helath | 0 1 2 3 4 5 6 7 |
| 13. Poor sleep had limited my ability to function and to cope during the day | 0 1 2 3 4 5 6 7 |
| 14. Poor sleep lead to low energy or feelings of tiredness or fatigue most of the day | 0 1 2 3 4 5 6 7 |
| 15. Poor sleep lead to trouble concnetrating or focusiing | 0 1 2 3 4 5 6 7 |
| 16. Poor sleep lead to feelings of depressed mood | 0 1 2 3 4 5 6 7 |
| 17. Poor sleep lead to irritability, tension, or or being on edge | 0 1 2 3 4 5 6 7 |
| 18. Poor sleep lead to having to push myself to get things done | 0 1 2 3 4 5 6 7 |
| 19. Poor sleep lead aches and pains (e.g. headaches, muscle achels, stomach ache) | 0 1 2 3 4 5 6 7 |

The sleep log includes both questions/statements rated on a scale, and questions/statements to which the response is a time period measured in hours and minutes. The sleep log includes the following questions/statements:

Sleep Log

Default sleep log (during baseline assessment and program):

1. Please rate the quality of your sleep last night:
   Using a scale of 1-5, very poor . . . excellent
2. How did you feel when you woke up this morning?
   Using a scale 1-5, exhausted . . . refreshed
3. What time did you turn off the light to go to sleep last night?
   →Enter time as hh:mm
4. How long did it take you to fall asleep?→Enter in minutes
5. What was the time when you finally woke up this morning?→Enter time as hh:mm
6. Please estimate the total amount of time (in minutes) you spent awake during the night (from the first time you fell asleep to the moment you finally woke up this morning) →Enter in minutes
7. What time did you get out of bed this morning?→Enter time as hh:mm
8. How tired did you feel yesterday?
   Using a scale of 1-5, very tired . . . very alert
9. Were there yesterday unusual external factors that may have disrupted your sleep?(e.g. health, work, family, environment, etc.)
   Using a scale of 1-5: many disruptive factors . . . no disruptive factors Another sleep assessment is the DBAS-16 which relates to a patient's beliefs about sleep and includes statements which the patient rates such as, but not limited to:

---

Several statements reflecting people's beliefs and attitudes about sleep are listed below. Please indicate to what extent you personally agree or disagree with each statement. There is no right or wrong answer. For each statement, circle the number that corresponds to your own personal belief. Please respond to all items even though some may not apply directly to your own situation.

Strongly Disagree                    Strongly Agree
0   1   2   3   4   5   6  (7)  8   9   10

1. I need 8 hours of sleep to feel refreshed and function well during the day.

0   1   2   3   4   5   6   7   8   9   10

2. When I don't get proper amount of sleep on a given night, I need to catch up on the next day by napping or on the next night by sleeping longer.

0   1   2   3   4   5   6   7   8   9   10

3. I am concerned that chronic insomnia may have serious consequences on my physical health.

0   1   2   3   4   5   6   7   8   9   10

4. I am worried that I may lose control over my abilities to sleep.

0   1   2   3   4   5   6   7   8   9   10

5. After a poor night's sleep, I know that it will interfere with the daily activities on the next day.

0   1   2   3   4   5   6   7   8   9   10

6. In order to be alert and function well during the day, I believe I would be better off taking a sleeping pill rather than having a poor night's sleep.

0   1   2   3   4   5   6   7   8   9   10

7. When feel irritable, depressed, or anxious during the day, it is mostly because I did not sleep well the night before.

0   1   2   3   4   5   6   7   8   9   10

8. When I sleep poorly on one night, I know it will disturb my sleep schedule for the whole week.

0   1   2   3   4   5   6   7   8   9   10

9. Without an adequate night's sleep, I can hardly function the next day.

0   1   2   3   4   5   6   7   8   9   10

10. I can't ever predict whether I'll have a good or poor night's sleep.

0   1   2   3   4   5   6   7   8   9   10

11. I have little ability to manage the negative consequences of disturbed sleep.

0   1   2   3   4   5   6   7   8   9   10

-continued

Several statements reflecting people's beliefs and attitudes about sleep are listed below. Please indicate to what extent you personally agree or disagree with each statement. There is no right or wrong answer. For each statement, circle the number that corresponds to your own personal belief. Please respond to all items even though some may not apply directly to your own situation.

Strongly Disagree                    Strongly Agree
0   1   2   3   4   5   6  (7)  8   9   10

12. When I feel tired, have no energy, or just seem not to function well during the day, it is generally because I did not sleep well the night before.

0   1   2   3   4   5   6   7   8   9   10

13. I believe insomnia is essentially the result of a chemical imbalance.

0   1   2   3   4   5   6   7   8   9   10

14. I feel insomnia is ruining my ability to enjoy life and prevents me from doing what I want.

0   1   2   3   4   5   6   7   8   9   10

15. Medication is probably the only solution to sleeplessness.

0   1   2   3   4   5   6   7   8   9   10

16. I avoid or cancel obligations (social, family) after a poor night's sleep.

0   1   2   3   4   5   6   7   8   9   10

---

Utilizing the system 1000 structured to facilitate cognitive behavioral therapy for a patient having insomnia the patient may receive cognitive behavioral therapy for insomnia according to a method having the following steps. Initially, the method includes the step of monitoring 2000 a patient's sleep utilizing a sensor system 1004 having at least one unobtrusive sensor 1020. As noted above, the sensor system 1004 is structured to detect sleeping activity data. The method further includes the steps of gathering 2002 patient input data, combining 2006 the patient input data and the sleeping activity data to create a patient sleep profile, analyzing 2008 a patient sleep profile to determine a course of therapy, and presenting 2010 the course of therapy to the patient on a display 1014.

The step of monitoring 2000 a patient's sleep utilizing a sensor system having at least one unobtrusive sensor includes the step of utilizing 2020 an ECG sensor and an actigraph sensor. As noted above, the ECG sensor 1022 is structured to detect heart rate data and respiratory rate data and the actigraph sensor 1024 is structured to detect patient body movement data. The step of monitoring 2000 a patient's sleep utilizing a sensor system having at least one unobtrusive sensor further includes the step of processing 2022 the heart rate data, respiratory rate data, and patient body movement data to determine at least one of: the patient's time in bed, the patient's total sleep time, the patient's total wake time, the patient's sleep efficiency, the patient's sleep onset latency, the patient's awakenings after sleep onset and the patient's snooze time.

The step of gathering 2002 patient input data includes the steps of: gathering 2030 data on the patient's sleep history, gathering 2032 data on the patient's medical history, having 2034 the patient complete an insomnia severity index assessment, and having 2036 the patient maintain a sleep log. As noted above, the patient input data is input via the second processing unit 2008 and, more specifically, via the input assembly 1034 and the user interface 108.

The step of analyzing 2008 a patient sleep profile to determine a course of therapy may include the steps of: analyzing 2038 the patient input data and the sleeping activity data to identify the factors contributing to the patients insomnia, identifying 2039 the type of insomnia associated with the patient, analyzing 2040 the patient input data and the sleeping activity data to determine the severity of the patient's insomnia, analyzing 2042 the patient input data to determine the severity of the effect of the patient's insomnia on daytime activities, analyzing 2044 the patient input data to determine the type of insomnia suffered by the patient, and, based on the severity of the patient's insomnia, the severity of the effect of the patient's insomnia on daytime activities, and the type of insomnia suffered by the patient, recommending 2046 to the patient one of the following: referral to a medical professional for treatment, recommending an interactive course of therapy to the patient, recommending no treatment.

If the patient is recommended an interactive course of therapy, the therapy is, preferably, provided to the patient via the display 1014 which presents the user interface 108. That is, the steps of analyzing 2008 the patient sleep profile to determine a course of therapy and presenting 2010 the course of therapy to the patient on a display 1014 include the steps of: providing 2050 a plurality of interactive therapeutic instruction modules, each module related to an aspect of insomnia, based on the patient sleep profile, determining 2052 which of the interactive therapeutic instruction modules are relevant to the patient's insomnia, determining 2054 the sequence of the interactive therapeutic instruction modules to be presented to the patient, presenting, 2056 in the predetermined sequence, the interactive therapeutic instruction modules to the patient on a display 1014.

As noted above, each interactive therapeutic instruction module 1060, 1062, 1064, 1066, 1068, 1070 contains three parts: (1) therapeutic advice, given on the first day a patient accesses a module, (2) the general information delivered in daily tips on the remaining days of the module, and (3) a goal setting section, accessible on the first day a patient accesses the module. The plurality of interactive therapeutic instruction modules include a sleep scheduling module 1060, an association bed-sleep module 1062, a cognitive restructuring module 1064, a coping strategy module 1066, a relaxation module 1068, and a lifestyle module 1070. In addition to the general information associated with each interactive therapeutic instruction module 1060, 1062, 1064, 1066, 1068, 1070, as discussed above, the specific modules each have additional processes as discussed below. It is further noted that the interactive therapeutic instruction modules 1060, 1062, 1064, 1066, 1068, 1070 may be (1) stored on the fourth processing unit 1012, i.e. in the storage device for the fourth processing unit 1012, (2) downloaded to the fourth processing unit 1012 via the electronic communication network 1001 and the communication assembly 1002, or (3) a combination thereof. That is, the fourth processing unit 1012 may store a portion of each interactive therapeutic instruction module 1060, 1062, 1064, 1066, 1068, 1070 and have updates or additional information downloaded as well.

For example, if the sleep scheduling module 1060 is recommended to the patient, the method of providing cognitive behavioral therapy for insomnia includes the further steps of: providing 2060 a sleep scheduling assessment structured to determine a first and a second sleep scheduling score, determining 2062 the patient's first and second sleep scheduling scores, and determining 2064 whether patient has an irregular sleep schedule. The determination 2062 of the patient's first and second sleep scheduling scores may be based on both objective and subjective data. For example, objective data, such as, but not limited to, sleep efficiency data collected by the sensors, as discussed above. Subjective data may be based on an assessment such as the following questions/statements:

I set myself a regular rising time each morning regardless of my sleep quality and duration (rated from strongly disagree to strongly agree);

When I don't get proper amount of sleep, on a given night, I need to catch up on the next day by napping or on the next night by sleeping longer (rated from strongly disagree to strongly agree); and Rating further translated into a score.

These ratings are converted into the patient's first and second sleep scheduling scores, e.g. by assigning a score to the answer and combining the score with objective data. Based on the factors that are determined, e.g. if patient's first sleep scheduling score is greater than a first sleep scheduling threshold value, the method further includes providing 2066 sleep schedule coaching, and/or, if the patient has an irregular sleep schedule and if patient's second sleep scheduling score is greater than a second sleep scheduling threshold value, providing 2068 sleep schedule coaching. In this module 1060, as well as all other modules 1062, 1064, 1066, 1068, 1070, the step of coaching is accomplished by providing information to the patient. Preferably, the information is provided via the display 1014 and in the form of text messages, e-mail, instant messages, etc. The coaching messages are, preferably, formatted as reminders, suggested therapeutic actions, progress reports, etc., and are typically related to a goal, as discussed above.

If the association bed-sleep module is recommended to the patient, the method of providing cognitive behavioral therapy for insomnia includes the further steps of: providing 2070 an association bed-sleep assessment structured to determine an association bed-sleep score, determining 2072 the patient's association bed-sleep score, and, if patient's association bed-sleep score is greater than an association bed-sleep threshold value, providing 2074 association bed-sleep coaching. The association bed-sleep assessment may include such questions/statements as:

Please indicate how often you do the following things in your bed before falling asleep or while in your bedroom. Complete the form by considering what you would do in an average week:

Watch TV, work, use the PC, listen to the radio or music, have a conversation with someone, speak on the telephone, eat and drink, read a book or magazine: never/rarely/sometimes/often/quite often;

I switch the light off as soon as I get into bed: never/rarely/sometimes/often/quite often; and I spend a lot of time lying awake in bed at night: never/rarely/sometimes/often/quite often which are converted into the patient's association bed-sleep score.

If the cognitive restructuring module 1064 is recommended to the patient, the method of providing cognitive behavioral therapy for insomnia includes the further steps of: providing 2080 a first sleep concept assessment structured to determine a first sleep concept score and determining 2082 the patient's first sleep concept score. If the patient's first sleep concept score is greater than a first sleep concept threshold value, performing 2084 a second sleep concept assessment to determine an amplification score, a perceived control score, and an unrealistic expectation score. Targeted coaching is provided related to any aspect of the sleep concept assessment wherein the patient is over the associated threshold value. That is, if patient's amplification score is greater than an amplification threshold value, providing 2086 amplification coaching. If the patient's perceived control score is greater than a perceived control threshold value, providing 2088 perceived control coaching. Further, if a patient's unrealistic expectation score is greater than an unrealistic expectation threshold value, providing 2089 unrealistic expectation coaching. The sleep concept assessment may include such questions/statements as:

Qa: "I put too much effort into sleeping at night when it should come naturally;"
Qb: "I worry about not sleeping if I am in bed at night and cannot sleep;" and
Qc: "I get anxious about sleeping before I go to bed at night"

as well as questions from the ISI, the IFQ and the DBAS-16 which are converted into a the patient's first and second sleep concept scores.

If the coping strategy module is recommended to the patient, the method of providing cognitive behavioral therapy for insomnia includes the further steps of: providing 2090 a first coping strategy assessment structured to determine a coping strategy score, determining 2092 a coping strategy score and, if patient's coping strategy score is greater than a coping strategy threshold value, providing 2094 coping strategy coaching. The coping strategy assessment may include such questions/statements as:

I have little ability to manage the negative consequences of disturbed sleep: never true, seldom true, sometimes true, often true, very often true;
I feel my sleep problems are ruining my ability to enjoy life and prevent me from doing what I want (social/occupational/family obligations); and
I avoid or cancel obligations (social, family) after a poor night's sleep which are converted into the patient's coping strategy score.

If the relaxation module is recommended to the patient, the method of providing cognitive behavioral therapy for insomnia includes the further steps of: providing 2100 a relaxation assessment structured to determine a transition time score, a worry time score, and a behavioral score, determining 2102 a transition time score, a worry time score, and a behavioral score. If the patient's transition time score is greater than a transition time threshold value, the method includes the step of providing 2104 transition time coaching. If the patient's worry time score is greater than a worry time threshold value, the method includes the step of providing 2106 worry time coaching. If the patient's behavioral score is greater than a behavioral threshold value, the method includes the step of providing 2108 behavioral coaching. The relaxation assessment may include such questions/statements as:

Q1: What do you usually do before going to bed? Watching TV, reading, working, using the PC, doing housework, other (checkboxes);
Q2: Would you consider your pre-bed activities as a routine? Yes/no;
Q3: How often do you experience one of the following problems while trying to fall asleep:
My mind keeps turning things over;
My thinking takes a long time to unwind; and
I am unable to empty my mind
(Never, seldom, sometimes, often, very often);
Q4: How often do you find it hard to physically "let go" and relax your body? Never, seldom, sometimes, often, very often;
Q5: How relaxed are you before going to bed? and
Q6: Do you think that stress/high workload makes your sleep poorer?
which are converted into the patient's relaxation score.

If the lifestyle module is recommended to the patient, the method of providing cognitive behavioral therapy for insomnia includes the further steps of: providing 2110 a lifestyle assessment structured to determine a physical activity score, an alcohol score, a caffeine score, a napping score, a nicotine score, an intake score (i.e. food and/or calorie intake score), and an environment score and determining 2111 a physical activity score, an alcohol score, a caffeine score, a napping score, a nicotine score, an intake score, and an environment score. If the patient's physical activity score is greater than a physical activity threshold value, the method includes the step of providing 2112 physical activity coaching. If the patient's alcohol score is greater than an alcohol threshold value, the method includes the step of providing 2114 alcohol coaching. If the patient's caffeine score is greater than a caffeine threshold value, the method includes the step of providing 2116 caffeine coaching. If the patient's napping score is greater than a napping threshold value, the method includes the step of providing 2118 napping coaching. If the patient's nicotine score is greater than a nicotine threshold value, the method includes the step of providing 2120 nicotine coaching. If the patient's intake score is greater than or less than the intake threshold value (or range), the method includes the step of providing 2122 intake coaching. That is, if the patient is eating too much or too little, the patient will be beyond the intake threshold range. If the patient's environment score is greater than an environment threshold value, the method includes the step of providing 2124 environment coaching. The lifestyle assessment may include, but is not limited to, such questions/statements as:

Q1: How often do you exercise and how long? X times per week, y minutes;
Q2: Do you exercise in the 4 hours preceding your bedtime?;
Q3: How many glasses of alcohol do you drink in the evening?
X glasses beer-wine-stronger (checkboxes);
Q4: How many cups of caffeinated drinks do you drink per day (coffee, tea, cola)? X cups, y of which in the evening;
Q5: Do you take naps? x times per week, y minutes;
Q6: When do you usually nap? Before/after 4 pm (checkboxes);
Q7: Do you smoke? x cigarettes per day;
Q8: Do you smoke before going to bed? In the middle of the night? Yes/no;
Q9: When you wake up during the night, you often:
Eat something?;
Have something to drink?; and
Got to the bathroom?
Q10: Do you have regular meal times?;
Q11: Do you feel sometimes too hot or too cold in your bed?;
Q12: Do you like your bedroom?;
Q13: Is your sleep sometimes disturbed by noise?; and
Q14: Is your sleep sometimes disturbed by light?
which are converted into the patient's physical activity score, an alcohol score, a caffeine score, a napping score, a nicotine score, an intake score, and an environment score.

As noted above, and as shown in FIG. 6, the method is, preferably, an iterative process wherein the patient's sleep profile is updated 2130 so as to reflect the patient's current level of insomnia. While the patient input data and the sleeping activity data may be updated every day, preferably the interactive course of therapy is updated regularly, but less frequently than daily. Preferably, the interactive course of therapy is updated weekly. Once the patient's patient sleep profile has been updated, the step of analyzing 2008 a patient sleep profile to determine a course of therapy is repeated. That is, the following steps, and any sub steps may be repeated: the steps of: analyzing 2040 the patient input data and the sleeping activity data to determine the severity of the patient's insomnia; analyzing 2042 the patient input data to determine the severity of the effect of the patient's insomnia on daytime activities; analyzing 2044 the patient input data to determine the type of insomnia suffered by the patient; and, based on the severity of the patient's insomnia, the severity of the effect of the patient's insomnia on daytime activities, and the type of insomnia suffered by the patient, recommending 2046 to the patient one of the following: referral to a medical professional for treatment; recommending an interactive course of therapy to the patient; and recommending no treatment.

Further, as the third processing unit 1010 is structured to send the sleep pattern data, the patient input data and the patient sleep profile to a medical professional via the electronic communications network 1001, the step of analyzing 2008 a patient sleep profile to determine a course of therapy may also include the steps of: having 2050 a medical professional review the sleep pattern data, the patient input data and the patient sleep profile, and having 2052 the medical professional provide direct feedback to the patient via the electronic communications network 1001. These steps may be repeated after an update of the sleep pattern data, the patient input data and the patient sleep profile.

One of ordinary skill in the art will appreciate many variations and modifications within the scope of this invention. This method and system will be used mainly for preferably insomnia patients at home or for patients at home or in hotels, for mobile patients in the hospital environment, during transport or at home but there are also applications possible for hospitalized patients. Also, devices could make use of this invention that are intended for healthy persons or even animals. Further, while the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A method of providing cognitive behavioral therapy for insomnia with a cognitive behavioral therapy system, the system comprising a communication assembly, a sensor system, one or more processing units, and a display, said method comprising the steps of:
   monitoring a patient's sleep with the communication assembly, the one or more processing units, and the sensor system, the sensor system having at least one unobstrusive sensor, said sensor system structured to detect sleeping activity data;
   gathering patient input data with the one or more processing units, at least one of the one or more processing units having an input assembly configured to gather patient input data, wherein the input data indicates a severity of an effect of the patient's insomnia on daytime activities;
   creating a patient sleep profile by combining, with the one or more processing units, said patient input data and said sleeping activity data;
   determining a course of therapy by analyzing, with the one or more processing units, said patient sleep profile; and
   presenting said course of therapy to said patient with the display.

2. The method of claim 1 wherein said step of monitoring a patient's sleep utilizing the sensor system having at least one unobtrusive sensor includes the steps of:
   utilizing an ECG sensor a respiration sensor, and an actigraph sensor, said ECG sensor structured to detect heart rate data, said respiration sensor structured to detect respiratory rate data, said actigraph sensor structured to detect patient body movement data; and
   processing, with the one or more processing units said heart rate data, respiratory rate data, and patient body movement data to determine at least one of said patient's time in bed, said patient's total sleep time, said patient's total wake time, said patient's sleep efficiency, said patient's sleep onset latency, said patient's awakenings after sleep onset and said patient's snooze time.

3. The method of claim 2 wherein said step of gathering patient input data with the one or more processing units includes the steps of:
   gathering data on said patient's sleep history;
   gathering data on said patient's medical history;
   having said patient complete an insomnia severity index; and
   having said patient maintain a sleep log.

4. The method of claim 3 wherein said step of analyzing said patient sleep profile to determine a course of therapy with the one or more processing units includes the steps of: analyzing said patient input data and said sleeping activity data to identify factors contributing to the patient's insomnia; and identifying a type of insomnia associated with the patient.

5. The method of claim 3 wherein said step of analyzing said patient sleep profile to determine a course of therapy with the one or more processing units includes the steps of:
   analyzing said patient input data and said sleeping activity data to determine the severity of the patient's insomnia;
   analyzing said patient input data to determine the severity of the effect of the patient's insomnia on daytime activities;
   analyzing said patient input data to determine which type of insomnia is suffered by the patient; and
   based on the severity of the patient's insomnia, the severity of the effect of the patient's insomnia on daytime activities, and the type of insomnia suffered by the patient, recommending to the patient one of the following: referral to a medical professional for treatment, recommending an interactive course of therapy to said patient, and recommending no treatment.

6. The method of claim 5 wherein, responsive to an interactive course of therapy being recommended, said steps of analyzing said patient sleep profile to determine a course of therapy with the one or more processing units and presenting said course of therapy to said patient with the display include the steps of:
provinding a plurality of interactive therapeutic instruction modules, wherein individual said modules are related to an aspect of insomnia;
based on said patient sleep profile, determining which of said interactive therapeutic instruction modules are relevant to the patient's insomnia;
determining a sequence of said interactive therapeutic instruction modules to be presented to said patient; and
presenting in said sequence, said interactive therapeutic instruction modules to said patient on the display.

7. The method of claim 6 wherein said plurality of interactive therapeutic instruction modules include a sleep scheduling module, an association bed-sleep module, a cognitive restructuring module, a coping strategy module, a relaxation module, and a lifestyle module.

8. The method of claim 7 wherein, responsive to said sleep scheduling module being recommended to the patient, said method of providing cognitive behavioral therapy for insomnia includes the further steps of:
providing a sleep scheduling assessment structured to determine a first and a second sleep scheduling score;
determining the patient's first and second sleep scheduling scores;
determining whether the patient has an irregular sleep schedule;
responsive to patient's first sleep scheduling score being greater that a first sleep scheduling threshold value, providing sleep schedule coaching; and
responsive to the patient having an irregular sleep schedule and the patient's second sleep scheduling score being greater than a second sleep scheduling threshold value, providing sleep schedule coaching.

9. The method of claim 7 wherein, responsive to said association bed-sleep module being recommended to the patient, said method of providing cognitive behavioral therapy for insomnia includes the further steps of;
providing an association bed-sleep assessment structured to determine an association bed-sleep score; and
responsive to the patient's association bed-sleep score being greater than an association bed-sleep threshold value, providing association bed-sleep coaching.

10. The method of claim 7 wherein, responsive to said cognitive restructuring module being recommended to the patient, said method of providing cognitive behavioral therapy for insomnia includes the further steps of:
providing a first sleep concept assessment structured to determine a first sleep concept score;
responsive to the patient'first sleep concept score being greater than a first sleep concept threshold value, performing a second sleep concept assessment to determine an amplification score, a perceived control score, and an expectation score;
responsive to the patient's amplification score greater than an amplification threshold value, providing amplification coaching;
responsive to the patient's perceived control score being greater than a perceived control threshold value, providing perceived control coaching; and
responsive to the patient's expectation score being greater than an expectation threshold value, providing expectation coaching.

11. The method of claim 7 wherein, responsive to said coping strategy module being recommended to the patient, said method of providing cognitive behavioral therapy for insomnia includes the further steps of:
providing a first coping strategy assessment structured to determine a coping strategy score; and
responsive to the patient's coping strategy score being greater than a coping strategy threshold value, providing coping strategy coaching.

12. The method of claim 7 wherein, responsive to said relaxation module being recommended to the patient, said method of providing cognitive behavioral therapy for insomnia includes the further steps of:
providing a relaxation assessment structured to determine a transition time score, a worry time score, and a behavioral score;
responsive to the patient's transition time score being greater than a transition time threshold value, providing transition time coaching;
responsive to the patient's worry time score being greater than a worry time threshold value, providing worry time coaching; and
responsive to the patient's behavioral score being greater than a behavioral threshold value, providing behavioral coaching.

13. The method of claim 7 wherein, responsive to said lifestyle module being recommended to the patient, said method of providing cognitive behavioral therapy for insomnia includes the further steps of:
providing a lifestyle assessment structured to determine a physical activity score, an alcohol score, a caffeine score, a napping score, a nicotine score. an intake score, and an environment score;
responsive to the patient's physical activity score being greater than a physical activity threshold value, providing physical activity coaching;
responsive to the patient's alcohol score being greater than an alcohol threshold value, providing alcohol coaching;
responsive to the patient's caffeine score being greater than a caffeine threshold value, providing caffeine coaching;
responsive to the patient's napping score being greater than a napping threshold value, providing napping coaching;
responsive to the patient's nicotine score being greater than a nicotine threshold value, providing nicotine coaching;
responsive to the patient's intake score being greater than an intake threshold value, providing intake coaching; and
responsive to the patient's environment score being greater than an environment threshold value, providing environment coaching.

14. The method of claim 6 wherein said step of analyzing said patient's sleep profile to determine a course of therapy with the one or more processing units includes the steps of:
updating the patient's patient sleep profile with data from said patient input data and said sleeping activity data; and
repeating the steps of:
analyzing said patient input data and said sleeping activity data to determine the severity of the patient's insomnia;
analyzing said patient input data to determine the severity of the effect of the patient's insomnia on daytime activities;

analyzing said patient input data to determine the type of insomnia suffered by the patient; and based on the severity of the patient's insomnia, the severity of the effect of the patient's insomnia on daytime activities, and the type of insomnia suffered by the patient, recommending to the patient one of the following: referral to a medical professional for treatment, recommending an interactive course of therapy to said patient, and recommending no treatment.

15. The method of claim 6 wherein said steps of analyzing said patient sleep profile to determine a course of therapy with the one or more processing units include at least one of the steps of:

having a medical professional review the sleep pattern data, the patient input data and the a patient sleep profile; and having said medical professional provide direct feedback to the patient via an electronic communications network.

* * * * *